US012679874B2

(12) United States Patent
Wang et al.

(10) Patent No.: US 12,679,874 B2
(45) Date of Patent: Jul. 14, 2026

(54) ELECTRICAL CONDUCTORS AND METHODS OF CONDUCTING IONS USING CALSEQUESTRIN PROTEINS

(71) Applicant: PEKING UNIVERSITY, Beijing (CN)

(72) Inventors: Shiqiang Wang, Beijing (CN); Xuexin Fan, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 1145 days.

(21) Appl. No.: 17/656,221

(22) Filed: Mar. 23, 2022

(65) Prior Publication Data

US 2022/0213157 A1    Jul. 7, 2022

Related U.S. Application Data

(63) Continuation of application No. PCT/CN2019/107535, filed on Sep. 24, 2019.

(51) Int. Cl.
C07K 14/47       (2006.01)
C08L 89/00       (2006.01)
G01N 27/414      (2006.01)

(52) U.S. Cl.
CPC .......... C07K 14/4728 (2013.01); C08L 89/00 (2013.01); G01N 27/4145 (2013.01)

(58) Field of Classification Search
CPC ................................................ C07K 14/4728
See application file for complete search history.

(56) References Cited

U.S. PATENT DOCUMENTS 9,804,121 B2    10/2017  Gorodetsky et al.
2013/0059905 A1   3/2013  Priori et al.
2015/0369805 A1  12/2015  Yang et al.

FOREIGN PATENT DOCUMENTS

CN    107265396 A    10/2017
CN    108319811 A     7/2018
EP     2755022 A1     7/2014
KR  20100089443 A     8/2010

OTHER PUBLICATIONS

Beard et al., "Calsequestrin and the calcium release channel of skeletal and cardiac muscle", Progress in Biophysics & Molecular Biology 85 (2004) 33-69.*
International Search Report in PCT/CN2019/107535 mailed on Jun. 24, 2020, 5 pages.
Written Opinion in PCT/CN2019/107535 mailed on Jun. 24, 2020, 4 pages.
Park, Hajeung et al., Comparing Skeletal and Cardiac Calsequestrin Structures and Their Calcium Binding, The Journal of Biological Chemistry, 279(17): 18026-18033, 2004.

Puspitapallab Chaudhuri et al., Conductance Through Glycine in a Graphene Nanogap, Journal of Nanoparticle Research, 20(158): 1-11, 2018.
A. Handhle et al., NCBI Reference Sequence: NP_001223.2 Calsequestrin-2 Precursor *Homo sapiens*, Genbank, 2019.
T.T. Aquilla et al., UniProtKB/Swiss-Prot: P51868.2 RecName: Full=Calsequestrin-2; AltName: Full=Calsequestrin, Cardiac Muscle Isoform; Flags: Precursor, Genbank, 2019.
Guan, Jianxin et al., Direct Single-molecule Dynamic Detection of Chemical Reactions, Science Advances, 4(2): 1-8, 2018.
Li, Yu et al., Single-Molecule Electrical Detection: A Promising Route toward the Fundamental Limits of Chemistry and Life Science, Accounts of Chemical Research, 53(1): 159-169, 2019.
Li, Linlin et al., Ultrastructural Quantification of Electron-Dense Strings in the Sarcoplasmic Reticulum of Rat Heart Cells, Biophysical Journal, 106(2): supplement 1, 2014.
Wang, Shiqiang et al., The Quantal Nature of Ca2+ Sparks and in Situ Operation of the Ryanodine Receptor Array in Cardiac Cells, Proceedings of the National Academy of Sciences of the United States of America, 101(11): 3979-3984, 2004.
Emiliano J. Sanchez, High-capacity Ca2+ Binding of Human Skeletal Calsequestrin, The Journal of Biological Chemistry, 287(14): 11592-11601, 2012.
Wang, Shuren et al., Crystal Structure of Calsequestrin from Rabbit Skeletal Muscle Sarcoplasmic Reticulum, Nature Structural Biology, 5(6): 476-483, 1998.
Kim, Eunjung et al., Characterization of Human Cardiac Calsequestrin and its Deleterious Mutants, Journal of Molecular Biology, 373(4): 1047-1057, 2007.
T. Wagenknecht et al., Electron Tomography of Frozen-Hydrated Isolated Triad Junctions, Biophysical Journal, 83(5): 2491-2501, 2002.
Xiang, Dong et al., Molecular-Scale Electronics: From Concept to Function, Chemical Reviews, 116(7): 4318-4440, 2015.
Naresh C. Bal et al., Probing Cationic Selectivity of Cardiac Calsequestrin and its CPVT Mutants, Biochem J. 435(2): 391-399, 2011.
Marta Gaburjakova et al., Functional Interaction Between Calsequestrin and Ryanodine Receptor in the Heart, Cellular and Molecular Life Sciences, 70(16): 2935-2945, 2013.
Hadas Lahat et al., A Missense Mutation in a Highly Conserved Region of CASQ2 is Asociated with Autosomal Recessive Catecholamine-induced Polymorphic Ventricular Tachycardia in Bedouin Families from Israel, American Journal of Human Genetics, 69(6): 1378-1384, 2001.
Sam De La Fuente et al., A Case of Catecholaminergic Polymorphic Ventricular Tachycardia Caused by Two Calsequestrin 2 Mutations, Pace-Pacing and Clinical Electrophysiology, 31(7): 916-919, 2008.

(Continued)

*Primary Examiner* — Suzanne M Noakes
(74) *Attorney, Agent, or Firm* — Metis IP LLC

(57)    ABSTRACT

An in vitro electrical conductor is provided. The in vitro electrical conductor may include a plurality of Calsequestrin (CSQ) protein molecules. The CSQ protein molecules may be connected to form a tendril, a network structure, or a biological tunnel structure. An electrical device including the in vitro electrical conductor is provided. An ionic transistor including the in vitro electrical conductor is provided. An in vitro method of conducting ions from an ion source to an ion sink is further provided. The method may include providing an electrical conductor including a plurality of CSQ protein molecules and conducting ions through the electrical conductor to the ion sink. The CSQ protein molecules may be connected to form a tendril, a network structure, or a biological tunnel structure.

18 Claims, 22 Drawing Sheets

Specification includes a Sequence Listing.

(56)　　　　　References Cited

OTHER PUBLICATIONS

Moonsub Shim et al., Functionalization of Carbon Nanotubes for Biocompatibility and Biomolecular Recognition, Nano letters, 2(4): 285-288, 2002.

Martyn D. Winn et al., Overview of the CCP4 Suite and Current Developments, Acta Crystallographica Section D. Biological Crystallography, D67: 235-242, 2011.

Paul D. Adams et al., Phenix: A Comprehensive Python-based System for Macromolecular Structure Solution, Acta Crystallographica Section D, Biological Crystallography, D66: 213-221, 2010.

P. Emsley et al., Features and Development of Coot, Acta Crystallographica Section D, Biological Crystallography, D66: 486-501, 2010.

* cited by examiner

Domain I

Domain III        Domain II

180°

Human rat

SEQUENCE LISTING

```
<160> NUMBER OF SEQ ID NOS: 9

<210> SEQ ID NO 1
<211> LENGTH: 380
<212> TYPE: PRT
<213> ORGANISM: Human

<400> SEQUENCE: 1

Glu Glu Gly Leu Asn Phe Pro Thr Tyr Asp Gly Lys Asp Arg Val Val
1               5                   10                  15

Ser Leu Ser Glu Lys Asn Phe Lys Gln Val Leu Lys Lys Tyr Asp Leu
            20                  25                  30

Leu Cys Leu Tyr Tyr His Glu Pro Val Ser Ser Asp Lys Val Thr Gln
        35                  40                  45

Lys Gln Phe Gln Leu Lys Glu Ile Val Leu Glu Leu Val Ala Gln Val
    50                  55                  60

Leu Glu His Lys Ala Ile Gly Phe Val Met Val Asp Ala Lys Lys Glu
65                  70                  75                  80
```

-continued

```
Ala Lys Leu Ala Lys Lys Leu Gly Phe Asp Glu Glu Gly Ser Leu Tyr
            85                  90                  95

Ile Leu Lys Gly Asp Arg Thr Ile Glu Phe Asp Gly Glu Phe Ala Ala
            100                 105                 110

Asp Val Leu Val Glu Phe Leu Leu Asp Leu Ile Glu Asp Pro Val Glu
            115                 120                 125

Ile Ile Ser Ser Lys Leu Glu Val Gln Ala Phe Glu Arg Ile Glu Asp
    130                 135                 140

Tyr Ile Lys Leu Ile Gly Phe Phe Lys Ser Glu Asp Ser Glu Tyr Tyr
145                 150                 155                 160

Lys Ala Phe Glu Glu Ala Ala Glu His Phe Gln Pro Tyr Ile Lys Phe
            165                 170                 175

Phe Ala Thr Phe Asp Lys Gly Val Ala Lys Lys Leu Ser Leu Lys Met
            180                 185                 190

Asn Glu Val Asp Phe Tyr Glu Pro Phe Met Asp Glu Pro Ile Ala Ile
            195                 200                 205

Pro Asn Lys Pro Tyr Thr Glu Glu Glu Leu Val Glu Phe Val Lys Glu
    210                 215                 220

His Gln Arg Pro Thr Leu Arg Arg Leu Arg Pro Glu Glu Met Phe Glu
225                 230                 235                 240

Thr Trp Glu Asp Asp Leu Asn Gly Ile His Ile Val Ala Phe Ala Glu
            245                 250                 255

Lys Ser Asp Pro Asp Gly Tyr Glu Phe Leu Glu Ile Leu Lys Gln Val
            260                 265                 270

Ala Arg Asp Asn Thr Asp Asn Pro Asp Leu Ser Ile Leu Trp Ile Asp
            275                 280                 285

Pro Asp Asp Phe Pro Leu Leu Val Ala Tyr Trp Glu Lys Thr Phe Lys
    290                 295                 300

Ile Asp Leu Phe Arg Pro Gln Ile Gly Val Val Asn Val Thr Asp Ala
305                 310                 315                 320

Asp Ser Val Trp Met Glu Ile Pro Asp Asp Asp Leu Pro Thr Ala
            325                 330                 335

Glu Glu Leu Glu Asp Trp Ile Glu Asp Val Leu Ser Gly Lys Ile Asn
            340                 345                 350

Thr Glu Asp Asp Asp Glu Asp Asp Asp Asp Asn Ser Asp Glu
            355                 360                 365

Glu Asp Asn Asp Asp Ser Asp Asp Asp Asp Glu
    370                 375                 380
```

```
<210> SEQ ID NO 2
<211> LENGTH: 394
<212> TYPE: PRT
<213> ORGANISM: Rat

<400> SEQUENCE: 2

Glu Glu Gly Leu Asn Phe Pro Thr Tyr Asp Gly Lys Asp Arg Val Val
1                   5                   10                  15

Ser Leu Ser Glu Lys Asn Leu Lys Gln Val Leu Lys Arg Tyr Asp Leu
            20                  25                  30

Leu Cys Leu Tyr Tyr His Glu Pro Val Ser Ser Asp Lys Val Ala Gln
            35                  40                  45

Lys Gln Phe Gln Leu Lys Glu Ile Val Leu Glu Leu Val Ala Gln Val
    50                  55                  60

Leu Glu His Lys Asn Ile Gly Phe Val Met Val Asp Ser Arg Lys Glu
```

```
65                  70                  75                  80

Ala Lys Leu Ala Lys Arg Leu Gly Phe Ser Glu Glu Gly Ser Leu Tyr
                85                  90                  95

Val Leu Lys Gly Gly Arg Thr Ile Glu Phe Asp Gly Glu Phe Ala Ala
            100                 105                 110

Asp Val Leu Val Glu Phe Leu Leu Asp Leu Ile Glu Asp Pro Val Glu
            115                 120                 125

Ile Val Asn Asn Lys Leu Glu Val Gln Ala Phe Glu Arg Ile Glu Asp
        130                 135                 140

Gln Ile Lys Leu Leu Gly Phe Phe Lys Asn Glu Asp Ser Glu Tyr Tyr
145                 150                 155                 160

Lys Ala Phe Gln Glu Ala Ala Glu His Phe Gln Pro Tyr Ile Lys Phe
                165                 170                 175

Phe Ala Thr Phe Asp Lys Gly Val Ala Lys Lys Leu Ser Leu Lys Met
            180                 185                 190

Asn Glu Val Gly Phe Tyr Glu Pro Phe Met Asp Glu Pro Ser Val Ile
            195                 200                 205

Pro Asn Lys Pro Tyr Thr Glu Glu Glu Leu Val Glu Phe Val Lys Glu
        210                 215                 220

His Gln Arg Pro Thr Leu Arg Pro Leu Arg Pro Glu Asp Met Phe Glu
225                 230                 235                 240

Thr Trp Glu Asp Asp Leu Asn Gly Ile His Ile Val Ala Phe Ala Glu
                245                 250                 255

Lys Ser Asp Pro Asp Gly Tyr Glu Phe Leu Glu Ile Leu Lys Gln Val
            260                 265                 270

Ala Arg Asp Asn Thr Asp Asn Pro Asp Leu Ser Ile Leu Trp Ile Asp
            275                 280                 285

Pro Asp Asp Phe Pro Leu Leu Val Ala Tyr Trp Glu Lys Thr Phe Lys
        290                 295                 300

Ile Asp Leu Phe Lys Pro Gln Ile Gly Val Val Asn Val Thr Asp Ala
305                 310                 315                 320

Asp Ser Val Trp Met Glu Ile Pro Asp Asp Asp Leu Pro Thr Ala
                325                 330                 335

Glu Glu Leu Glu Asp Trp Ile Glu Asp Val Leu Ser Gly Lys Ile Asn
            340                 345                 350

Thr Glu Asp Asp Asp Asn Glu Asp Glu Asp Asp Gly Asp Asn Asp
            355                 360                 365

Asn Asp Asp Asp Asp Asp Asp Asp Asn Asp Asp Glu Asp Asn Asp
        370                 375                 380

Asp Asp Asp Asp Asp Asp Asp Asp Glu
385                 390
```

```
<210> SEQ ID NO 3
<211> LENGTH: 398
<212> TYPE: PRT
<213> ORGANISM: Human

<400> SEQUENCE: 3

Met Lys Arg Thr His Leu Phe Ile Val Gly Ile Tyr Phe Leu Ser Ser
1               5                   10                  15

Cys Arg Ala Glu Glu Gly Leu Asn Phe Pro Thr Tyr Asp Gly Lys Asp
            20                  25                  30

Arg Val Val Ser Leu Ser Glu Lys Asn Phe Lys Gln Val Leu Lys Lys
        35                  40                  45
```

```
Tyr Asp Leu Leu Cys Leu Tyr Tyr His Glu Pro Val Ser Ser Asp Lys
    50              55                  60

Val Thr Gln Lys Gln Phe Gln Leu Lys Glu Ile Val Leu Glu Leu Val
65              70                  75                  80

Ala Gln Val Leu Glu His Lys Ala Ile Gly Phe Val Met Val Asp Ala
                85                  90                  95

Lys Lys Glu Ala Lys Leu Ala Lys Lys Leu Gly Phe Asp Glu Glu Gly
            100                 105                 110

Ser Leu Tyr Ile Leu Lys Gly Asp Arg Thr Ile Glu Phe Asp Gly Glu
        115                 120                 125

Phe Ala Ala Asp Val Leu Val Glu Phe Leu Leu Asp Leu Ile Glu Asp
    130                 135                 140

Pro Val Glu Ile Ile Ser Ser Lys Leu Glu Val Gln Ala Phe Glu Arg
145                 150                 155                 160

Ile Glu Asp Tyr Ile Lys Leu Ile Gly Phe Phe Lys Ser Glu Asp Ser
                165                 170                 175

Glu Tyr Tyr Lys Ala Phe Glu Glu Ala Ala Glu His Phe Gln Pro Tyr
            180                 185                 190

Ile Lys Phe Phe Ala Thr Phe Asp Lys Gly Val Ala Lys Lys Leu Ser
        195                 200                 205

Leu Lys Met Asn Glu Val Asp Phe Tyr Glu Pro Phe Met Asp Glu Pro
    210                 215                 220

Ile Ala Ile Pro Asn Lys Pro Tyr Thr Glu Glu Glu Leu Val Glu Phe
225                 230                 235                 240

Val Lys Glu His Gln Arg Pro Thr Leu Arg Arg Leu Arg Pro Glu Glu
                245                 250                 255

Met Phe Glu Thr Trp Glu Asp Asp Leu Asn Gly Ile His Ile Val Ala
            260                 265                 270

Phe Ala Glu Lys Ser Asp Pro Asp Gly Tyr Glu Phe Leu Glu Ile Leu
        275                 280                 285

Lys Gln Val Ala Arg Asp Asn Thr Asp Asn Pro Asp Leu Ser Ile Leu
    290                 295                 300

Trp Ile Asp Pro Asp Asp Phe Pro Leu Leu Val Ala Tyr Trp Glu Lys
305                 310                 315                 320

Thr Phe Lys Ile Asp Leu Phe Arg Pro Gln Ile Gly Val Val Asn Val
                325                 330                 335

Thr Asp Ala Asp Ser Val Trp Met Glu Ile Pro Asp Asp Asp Asp Leu
            340                 345                 350

Pro Thr Ala Glu Glu Leu Glu Asp Trp Ile Glu Asp Val Leu Ser Gly
        355                 360                 365

Lys Ile Asn Thr Glu Asp Asp Asp Glu Asp Asp Asp Asp Asp Asp Asn
    370                 375                 380

Ser Asp Glu Glu Asp Asn Asp Asp Ser Asp Asp Asp Asp
385                 390                 395

<210> SEQ ID NO 4
<211> LENGTH: 404
<212> TYPE: PRT
<213> ORGANISM: Rat

<400> SEQUENCE: 4

Met Lys Arg Ile Tyr Leu Leu Val Val Gly Leu Tyr Leu Leu Ser Phe
1               5                   10                  15

Ser Arg Ala Glu Glu Gly Leu Asn Phe Pro Thr Tyr Asp Gly Lys Asp
            20                  25                  30
```

-continued

```
Arg Val Val Ser Leu Ser Glu Lys Asn Leu Lys Gln Val Leu Lys Arg
        35                  40                  45

Tyr Asp Leu Leu Cys Leu Tyr Tyr His Glu Pro Val Ser Ser Asp Lys
    50                  55                  60

Val Ala Gln Lys Gln Phe Gln Leu Lys Glu Ile Val Leu Glu Leu Val
65                  70                  75                  80

Ala Gln Val Leu Glu His Lys Asn Ile Gly Phe Val Met Val Asp Ser
                85                  90                  95

Arg Lys Glu Ala Lys Leu Ala Lys Arg Leu Gly Phe Ser Glu Glu Gly
                100                 105                 110

Ser Leu Tyr Val Leu Lys Gly Gly Arg Thr Ile Glu Phe Asp Gly Glu
            115                 120                 125

Phe Ala Ala Asp Val Leu Val Glu Phe Leu Leu Asp Leu Ile Glu Asp
        130                 135                 140

Pro Val Glu Ile Val Asn Asn Lys Leu Glu Val Gln Ala Phe Glu Arg
145                 150                 155                 160

Ile Glu Asp Gln Ile Lys Leu Leu Gly Phe Phe Lys Asn Glu Asp Ser
                165                 170                 175

Glu Tyr Tyr Lys Ala Phe Gln Glu Ala Ala Glu His Phe Gln Pro Tyr
            180                 185                 190

Ile Lys Phe Phe Ala Thr Phe Asp Lys Gly Val Ala Lys Lys Leu Ser
            195                 200                 205

Leu Lys Met Asn Glu Val Gly Phe Tyr Glu Pro Phe Met Asp Glu Pro
    210                 215                 220

Ser Val Ile Pro Asn Lys Pro Tyr Thr Glu Glu Glu Leu Val Glu Phe
225                 230                 235                 240

Val Lys Glu His Gln Arg Pro Thr Leu Arg Pro Leu Arg Pro Glu Asp
                245                 250                 255

Met Phe Glu Thr Trp Glu Asp Asp Leu Asn Gly Ile His Ile Val Ala
            260                 265                 270

Phe Ala Glu Lys Ser Asp Pro Asp Gly Tyr Glu Phe Leu Glu Ile Leu
        275                 280                 285

Lys Gln Val Ala Arg Asp Asn Thr Asp Asn Pro Asp Leu Ser Ile Leu
    290                 295                 300

Trp Ile Asp Pro Asp Asp Phe Pro Leu Leu Val Ala Tyr Trp Glu Lys
305                 310                 315                 320

Thr Phe Lys Ile Asp Leu Phe Lys Pro Gln Ile Gly Val Val Asn Val
            325                 330                 335

Thr Asp Ala Asp Ser Val Trp Met Glu Ile Pro Asp Asp Asp Asp Leu
            340                 345                 350

Pro Thr Ala Glu Glu Leu Glu Asp Trp Ile Glu Asp Val Leu Ser Gly
            355                 360                 365

Lys Ile Asn Thr Glu Asp Asp Asp Asn Glu Asp Glu Asp Asp Asp Gly
    370                 375                 380

Asp Asn Asp Asn Asp Asp Asp Asp Asp Asp Asp Asn Ser Asp Glu
385                 390                 395                 400

Asp Asn Asp Asp
```

<210> SEQ ID NO 5
<211> LENGTH: 403
<212> TYPE: PRT
<213> ORGANISM: Rabbit

<400> SEQUENCE: 5

-continued

```
Met Lys Arg Ala His Leu Phe Val Val Gly Val Tyr Leu Leu Ser Ser
1               5                   10                  15

Cys Arg Ala Glu Glu Gly Leu Asn Phe Pro Thr Tyr Asp Gly Lys Asp
                20                  25                  30

Arg Val Val Ser Leu Ser Glu Lys Asn Phe Lys Gln Ile Leu Lys Lys
            35                  40                  45

Tyr Asp Leu Leu Cys Leu Tyr Tyr His Ala Pro Val Ser Ala Asp Lys
        50                  55                  60

Val Ala Gln Lys Gln Phe Gln Leu Lys Glu Ile Val Leu Glu Leu Val
65                  70                  75                  80

Ala Gln Val Leu Glu His Lys Glu Ile Gly Phe Val Met Val Asp Ala
                85                  90                  95

Lys Lys Glu Ala Lys Leu Ala Lys Lys Leu Gly Phe Asp Glu Glu Gly
            100                 105                 110

Ser Leu Tyr Ile Leu Lys Gly Asp Arg Thr Ile Glu Phe Asp Gly Glu
        115                 120                 125

Phe Ala Ala Asp Val Leu Val Glu Phe Leu Leu Asp Leu Ile Glu Asp
        130                 135                 140

Pro Val Glu Ile Ile Asn Ser Lys Leu Glu Val Gln Ala Phe Glu Arg
145                 150                 155                 160

Ile Glu Asp His Ile Lys Leu Ile Gly Phe Phe Lys Ser Ala Asp Ser
                165                 170                 175

Glu Tyr Tyr Lys Ala Phe Glu Glu Ala Ala Glu His Phe Gln Pro Tyr
                180                 185                 190

Ile Lys Phe Phe Ala Thr Phe Asp Lys Gly Val Ala Lys Lys Leu Ser
            195                 200                 205

Leu Lys Met Asn Glu Val Asp Phe Tyr Glu Pro Phe Met Asp Glu Pro
        210                 215                 220

Thr Pro Ile Pro Asn Lys Pro Tyr Thr Glu Glu Glu Leu Val Glu Phe
225                 230                 235                 240

Val Lys Glu His Gln Arg Pro Thr Leu Arg Arg Leu Arg Pro Glu Asp
                245                 250                 255

Met Phe Glu Thr Trp Glu Asp Asp Leu Asn Gly Ile His Ile Val Pro
            260                 265                 270

Phe Ala Glu Lys Ser Asp Pro Asp Gly Tyr Glu Phe Leu Glu Ile Leu
            275                 280                 285

Lys Gln Val Ala Arg Asp Asn Thr Asp Asn Pro Asp Leu Ser Ile Val
        290                 295                 300

Trp Ile Asp Pro Asp Asp Phe Pro Leu Leu Val Ala Tyr Trp Glu Lys
305                 310                 315                 320

Thr Phe Lys Ile Asp Leu Phe Lys Pro Gln Ile Gly Val Val Asn Val
            325                 330                 335

Thr Asp Ala Asp Ser Val Trp Met Glu Ile Pro Asp Asp Asp Asp Leu
            340                 345                 350

Pro Thr Ala Glu Glu Leu Glu Asp Trp Ile Glu Asp Val Leu Ser Gly
        355                 360                 365

Lys Ile Asn Thr Glu Asp Asp Asp Asn Glu Asp Glu Asp Asp Asp Asp
        370                 375                 380

Asp Asn Asp Asp Asp Asp Asp Asp Asn Gly Asn Ser Asp Glu Glu Asp
385                 390                 395                 400

Asn Asp Asp
```

-continued

```
<210> SEQ ID NO 6
<211> LENGTH: 404
<212> TYPE: PRT
<213> ORGANISM: dog

<400> SEQUENCE: 6

Met Lys Arg Thr His Leu Phe Ile Ala Gly Leu Tyr Leu Leu Ala Ser
1               5                   10                  15

Cys Arg Ala Glu Glu Gly Leu Asn Phe Pro Thr Tyr Asp Gly Lys Asp
                20                  25                  30

Arg Val Val Ser Leu Thr Glu Lys Asn Phe Lys Gln Val Leu Lys Lys
                35                  40                  45

Tyr Asp Val Leu Cys Leu Tyr Tyr His Glu Ser Val Ser Ser Asp Lys
        50                  55                  60

Val Ala Gln Lys Gln Phe Gln Leu Lys Glu Ile Val Leu Glu Leu Val
65                  70                  75                  80

Ala Gln Val Leu Glu His Lys Asp Ile Gly Phe Val Met Val Asp Ala
                85                  90                  95

Lys Lys Glu Ala Lys Leu Ala Lys Lys Leu Gly Phe Asp Glu Glu Gly
                100                 105                 110

Ser Leu Tyr Val Leu Lys Gly Asp Arg Thr Ile Glu Phe Asp Gly Glu
        115                 120                 125

Phe Ala Ala Asp Val Leu Val Glu Phe Leu Leu Asp Leu Ile Glu Asp
        130                 135                 140

Pro Val Glu Ile Ile Asn Ser Lys Leu Glu Val Gln Ala Phe Glu Arg
145                 150                 155                 160

Ile Glu Asp Gln Ile Lys Leu Ile Gly Phe Phe Lys Ser Glu Glu Ser
                165                 170                 175

Glu Tyr Tyr Lys Ala Phe Glu Glu Ala Ala Glu His Phe Gln Pro Tyr
                180                 185                 190

Ile Lys Phe Phe Ala Thr Phe Asp Lys Gly Val Ala Lys Lys Leu Ser
        195                 200                 205

Leu Lys Met Asn Glu Val Asp Phe Tyr Glu Pro Phe Met Asp Glu Pro
        210                 215                 220

Ile Ala Ile Pro Asp Lys Pro Tyr Thr Glu Glu Glu Leu Val Glu Phe
225                 230                 235                 240

Val Lys Glu His Gln Arg Pro Thr Leu Arg Arg Leu Arg Pro Glu Asp
                245                 250                 255

Met Phe Glu Thr Trp Glu Asp Asp Leu Asn Gly Ile His Ile Val Ala
                260                 265                 270

Phe Ala Glu Arg Ser Asp Pro Asp Gly Tyr Glu Phe Leu Glu Ile Leu
        275                 280                 285

Lys Gln Val Ala Arg Asp Asn Thr Asp Asn Pro Asp Leu Ser Ile Val
        290                 295                 300

Trp Ile Asp Pro Asp Asp Phe Pro Leu Leu Val Ala Tyr Trp Glu Lys
305                 310                 315                 320

Thr Phe Lys Ile Asp Leu Phe Lys Pro Gln Ile Gly Val Val Asn Val
                325                 330                 335

Thr Asp Ala Asp Ser Val Trp Met Glu Ile Pro Asp Asp Asp Leu
                340                 345                 350

Pro Thr Ala Glu Glu Leu Glu Asp Trp Ile Glu Asp Val Leu Ser Gly
        355                 360                 365

Lys Ile Asn Thr Glu Asp Asp Asp Asn Glu Glu Gly Asp Asp Gly Asp
        370                 375                 380
```

-continued

```
Asp Asp Glu Asp Asp Asp Asp Asp Gly Asn Asn Ser Asp Glu Glu
385             390             395             400

Ser Asn Asp Asp

<210> SEQ ID NO 7
<211> LENGTH: 395
<212> TYPE: PRT
<213> ORGANISM: Human

<400> SEQUENCE: 7

Met Ser Ala Thr Asp Arg Met Gly Pro Arg Ala Val Pro Gly Leu Arg
1               5               10              15

Leu Ala Leu Leu Leu Leu Leu Val Leu Gly Thr Pro Lys Ser Gly Val
            20              25              30

Gln Gly Gln Glu Gly Leu Asp Phe Pro Glu Tyr Asp Gly Val Asp Arg
        35              40              45

Val Ile Asn Val Asn Ala Lys Asn Tyr Lys Asn Val Phe Lys Lys Tyr
    50              55              60

Glu Val Leu Ala Leu Leu Tyr His Glu Pro Pro Glu Asp Asp Lys Ala
65              70              75              80

Ser Gln Arg Gln Phe Glu Met Glu Glu Leu Ile Leu Glu Leu Ala Ala
            85              90              95

Gln Val Leu Glu Asp Lys Gly Val Gly Phe Gly Leu Val Asp Ser Glu
        100             105             110

Lys Asp Ala Ala Val Ala Lys Lys Leu Gly Leu Thr Glu Val Asp Ser
        115             120             125

Met Tyr Val Phe Lys Gly Asp Glu Val Ile Glu Tyr Asp Gly Glu Phe
    130             135             140

Ser Ala Asp Thr Ile Val Glu Phe Leu Leu Asp Val Leu Glu Asp Pro
145             150             155             160

Val Glu Leu Ile Glu Gly Glu Arg Glu Leu Gln Ala Phe Glu Asn Ile
            165             170             175

Glu Asp Glu Ile Lys Leu Ile Gly Tyr Phe Lys Ser Lys Asp Ser Glu
        180             185             190

His Tyr Lys Ala Phe Glu Asp Ala Ala Glu Glu Phe His Pro Tyr Ile
        195             200             205

Pro Phe Phe Ala Thr Phe Asp Ser Lys Val Ala Lys Lys Leu Thr Leu
    210             215             220

Lys Leu Asn Glu Ile Asp Phe Tyr Glu Ala Phe Met Glu Glu Pro Val
225             230             235             240

Thr Ile Pro Asp Lys Pro Asn Ser Glu Glu Glu Ile Val Asn Phe Val
            245             250             255

Glu Glu His Arg Arg Ser Thr Leu Arg Lys Leu Lys Pro Glu Ser Met
        260             265             270

Tyr Glu Thr Trp Glu Asp Asp Met Asp Gly Ile His Ile Val Ala Phe
    275             280             285

Ala Glu Glu Ala Asp Pro Asp Gly Phe Glu Phe Leu Glu Thr Leu Lys
    290             295             300

Ala Val Ala Gln Asp Asn Thr Glu Asn Pro Asp Leu Ser Ile Ile Trp
305             310             315             320

Ile Asp Pro Asp Asp Phe Pro Leu Leu Val Pro Tyr Trp Glu Lys Thr
            325             330             335

Phe Asp Ile Asp Leu Ser Ala Pro Gln Ile Gly Val Val Asn Val Thr
        340             345             350
```

```
Asp Ala Asp Ser Val Trp Met Glu Met Asp Asp Glu Glu Asp Leu Pro
        355             360             365

Ser Ala Glu Glu Leu Glu Asp Trp Leu Glu Asp Val Leu Glu Gly Glu
        370             375             380

Ile Asn Thr Glu Asp Asp Asp Asp Asp Asp
385             390             395

<210> SEQ ID NO 8
<211> LENGTH: 405
<212> TYPE: PRT
<213> ORGANISM: Rat

<400> SEQUENCE: 8

Met Arg Ala Thr Asp Arg Met Gly Ala Arg Ala Val Ser Lys Leu Arg
1               5               10              15

Leu Ala Leu Leu Phe Val Leu Val Leu Gly Thr Pro Arg Ser Gly Val
        20              25              30

Gln Gly Glu Asp Gly Leu Asp Phe Pro Glu Tyr Asp Gly Val Asp Arg
        35              40              45

Val Ile Asn Val Asn Ala Lys Asn Tyr Lys Asn Val Phe Lys Lys Tyr
    50              55              60

Glu Val Leu Ala Leu Leu Tyr His Glu Pro Pro Glu Asp Asp Lys Ala
65              70              75              80

Ser Gln Arg Gln Phe Glu Met Glu Glu Leu Ile Leu Glu Leu Ala Ala
            85              90              95

Gln Val Leu Glu Asp Lys Gly Val Gly Phe Gly Leu Val Asp Ser Glu
        100             105             110

Lys Asp Ala Ala Val Ala Lys Lys Leu Gly Leu Thr Glu Glu Asp Ser
        115             120             125

Val Tyr Val Phe Lys Gly Asp Glu Val Ile Glu Tyr Asp Gly Glu Phe
    130             135             140

Ser Ala Asp Thr Leu Val Glu Phe Leu Leu Asp Val Leu Glu Asp Pro
145             150             155             160

Val Glu Leu Ile Glu Gly Glu Arg Glu Leu Gln Ala Phe Glu Asn Ile
            165             170             175

Glu Asp Glu Ile Lys Leu Ile Gly Tyr Phe Lys Ser Lys Asp Ser Glu
        180             185             190

His Tyr Lys Ala Tyr Glu Asp Ala Ala Glu Glu Phe His Pro Tyr Ile
        195             200             205

Pro Phe Phe Ala Thr Phe Asp Ser Lys Val Ala Lys Lys Leu Thr Leu
    210             215             220

Lys Leu Asn Glu Ile Asp Phe Tyr Glu Ala Phe Met Glu Glu Pro Val
225             230             235             240

Thr Ile Pro Asp Lys Pro Asn Ser Glu Glu Glu Ile Val Ser Phe Val
            245             250             255

Glu Glu His Arg Arg Ser Thr Leu Arg Lys Leu Lys Pro Glu Ser Met
        260             265             270

Tyr Glu Thr Trp Glu Asp Asp Leu Asp Gly Ile His Ile Val Ala Phe
        275             280             285

Ala Glu Glu Ala Asp Pro Asp Gly Tyr Glu Phe Leu Glu Thr Leu Lys
        290             295             300

Ala Val Ala Gln Asp Asn Thr Glu Asn Pro Asp Leu Ser Ile Ile Trp
305             310             315             320

Ile Asp Pro Asp Asp Phe Pro Leu Leu Val Pro Tyr Trp Glu Lys Thr
            325             330             335
```

-continued

```
Phe Asp Ile Asp Leu Ser Ala Pro Gln Ile Gly Val Val Asn Val Thr
            340                 345                 350

Asp Ala Asp Ser Ile Trp Met Glu Met Asp Asp Glu Glu Asp Leu Pro
            355                 360                 365

Ser Ala Glu Glu Leu Glu Asp Trp Leu Glu Asp Val Leu Glu Gly Glu
            370                 375                 380

Ile Asn Thr Glu Asp Asp Asp Asp Asp Asp Asp Asp Asp Asp Asp Asp
385                 390                 395                 400

Asp Asp Asp Asp Asp
            405

<210> SEQ ID NO 9
<211> LENGTH: 394
<212> TYPE: PRT
<213> ORGANISM: rabbit

<400> SEQUENCE: 9

Met Asn Ala Ala Asp Arg Met Gly Ala Arg Val Ala Leu Leu Leu Leu
1               5                   10                  15

Leu Val Leu Gly Ser Pro Gln Ser Gly Val His Gly Glu Glu Gly Leu
            20                  25                  30

Asp Phe Pro Glu Tyr Asp Gly Val Asp Arg Val Ile Asn Val Asn Ala
            35                  40                  45

Lys Asn Tyr Lys Asn Val Phe Lys Lys Tyr Glu Val Leu Ala Leu Leu
            50                  55                  60

Tyr His Glu Pro Pro Glu Asp Asp Lys Ala Ser Gln Arg Gln Phe Glu
65                  70                  75                  80

Met Glu Glu Leu Ile Leu Glu Leu Ala Ala Gln Val Leu Glu Asp Lys
                85                  90                  95

Gly Val Gly Phe Gly Leu Val Asp Ser Glu Lys Asp Ala Ala Val Ala
            100                 105                 110

Lys Lys Leu Gly Leu Thr Glu Glu Asp Ser Ile Tyr Val Phe Lys Glu
            115                 120                 125

Asp Glu Val Ile Glu Tyr Asp Gly Glu Phe Ser Ala Asp Thr Leu Val
            130                 135                 140

Glu Phe Leu Leu Asp Val Leu Glu Asp Pro Val Glu Leu Ile Glu Gly
145                 150                 155                 160

Glu Arg Glu Leu Gln Ala Phe Glu Asn Ile Glu Asp Glu Ile Lys Leu
            165                 170                 175

Ile Gly Tyr Phe Lys Asn Lys Asp Ser Glu His Tyr Lys Ala Phe Lys
            180                 185                 190

Glu Ala Ala Glu Glu Phe His Pro Tyr Ile Pro Phe Phe Ala Thr Phe
            195                 200                 205

Asp Ser Lys Val Ala Lys Lys Leu Thr Leu Lys Leu Asn Glu Ile Asp
            210                 215                 220

Phe Tyr Glu Ala Phe Met Glu Glu Pro Val Thr Ile Pro Asp Lys Pro
225                 230                 235                 240

Asn Ser Glu Glu Glu Ile Val Asn Phe Val Glu Glu His Arg Arg Ser
            245                 250                 255

Thr Leu Arg Lys Leu Lys Pro Glu Ser Met Tyr Glu Thr Trp Glu Asp
            260                 265                 270

Asp Met Asp Gly Ile His Ile Val Ala Phe Ala Glu Glu Ala Asp Pro
            275                 280                 285

Asp Gly Tyr Glu Phe Leu Glu Ile Leu Lys Ser Val Ala Gln Asp Asn
```

-continued

```
        290              295              300

Thr Asp Asn Pro Asp Leu Ser Ile Ile Trp Ile Asp Pro Asp Phe
305              310              315              320

Pro Leu Leu Val Pro Tyr Trp Glu Lys Thr Phe Asp Ile Asp Leu Ser
            325              330              335

Ala Pro Gln Ile Gly Val Val Asn Val Thr Asp Ala Asp Ser Val Trp
            340              345              350

Met Glu Met Asp Asp Glu Glu Asp Leu Pro Ser Ala Glu Glu Leu Glu
        355              360              365

Asp Trp Leu Glu Asp Val Leu Glu Gly Glu Ile Asn Thr Glu Asp Asp
    370              375              380

Asp Asp Glu Asp Asp Asp Asp Asp Asp
385              390
```

ELECTRICAL CONDUCTORS AND METHODS OF CONDUCTING IONS USING CALSEQUESTRIN PROTEINS

CROSS-REFERENCE TO RELATED APPLICATIONS

This application is a continuation of International Application No. PCT/CN2019/107535, filed on Sep. 24, 2019, which designates the United States of America, the contents of which are incorporated herein by reference in their entirety.

SEQUENCE LISTING

The instant application contains a Sequence Listing which has been submitted electronically in SEQ.TXT format and is hereby incorporated by reference in its entirety. The SEQ.TXT file, created on Mar. 23, 2022, is named "Sequence listing-20314-0001 US00," and is 31,240 bytes in size.

TECHNICAL FIELD

The present disclosure generally relates to molecular biology and electronics, and in particular, to electrical conductors including calsequestrin (CSQ) proteins and methods of conducting ions through CSQ protein molecules.

BACKGROUND

An electrical conductor usually refers to an object that allows the flow of an electrical current. The electrical current can be generated by the flow of electrons, ions, or a combination thereof. An electronic device may include one or more electrical conductors to implement a certain function, such as generating light, generating heat, detecting signals, transmitting signals, moving, etc. In some applications, the electronic device may be designed with a small size, such as a chip, a biomedical implantable device. Such an electronic device may be built based on micrometer-scale or nanometer-scale electrical conductors.

Proteins or peptides are natural biomolecules having a micrometer-scale or nanometer-scale size, which makes proteins or peptides a suitable material for producing a microstructure or a nanostructure. CSQ is a protein capable of cyclically binding and releasing calcium ions ($Ca^{2+}$) in an excitation-contraction coupling of muscles. The CSQ protein may aggregate into dimers, tetramers, etc., and form a negatively charged structure for binding $Ca^{2+}$. Therefore, it is desirable to provide electrical conductors including CSQ proteins and methods of conducting ions using a plurality of CSQ proteins.

SUMMARY

According to an aspect of the present disclosure, an in vitro electrical conductor is provided.

In some embodiments, the CSQ protein molecules may include CSQ1 molecules that use intermolecular interactions to form the tendril or the network structure.

In some embodiments, the CSQ protein molecules may form a biological tunnel structure including a CSQ protein dimer, wherein the CSQ protein dimer includes two CSQ molecules either of which is a CSQ1 molecule or a CSQ2 molecule.

In some embodiments, the CSQ protein dimer may include two CSQ1 molecules using an intermolecular interaction to form the biological tunnel structure.

In some embodiments, the CSQ protein dimer includes two CSQ2 molecules using an intermolecular interaction to form the biological tunnel structure.

In some embodiments, at least one of the CSQ2 protein molecules may include an amino acid sequence with at least 95% similarity to SEQ ID NO: 1, which consists of human CSQ2 protein sequence without amino acids 1-19.

In some embodiments, at least one of the CSQ2 protein molecules may consist of an amino acid sequence with at least 99% similarity to SEQ ID NO: 1, which consists of human CSQ2 protein sequence without amino acids 1-19.

In some embodiments, at least one of the CSQ2 protein molecules may include an amino acid sequence with at least 95% similarity to SEQ ID NO: 2, which consists of rat CSQ2 protein sequence without amino acids 1-19.

In some embodiments, at least one of the CSQ2 protein molecules may consist of an amino acid sequence with at least 99% similarity to SEQ ID NO: 2, which consists of rat CSQ2 protein sequence without amino acids 1-19.

In some embodiments, at least one of the CSQ2 protein molecules may include one or more amino acid mutations that enhance or reduce conductivity of the biological tunnel structure.

In some embodiments, at least one of the CSQ2 protein molecules may include a mutation of D (Asp) to N (Asn) at amino acid position 309 as defined in a full-length human or rat CSQ2 protein sequence.

In some embodiments, at least one of the CSQ2 protein molecules includes a D (Asp) to C (Cys) mutation, which facilitates a connection between the biological tunnel structure to an exterior member.

In some embodiments, the D (Asp) to C (Cys) mutation is at amino acid position 348 as defined in a full-length human or rat CSQ2 protein sequence.

In some embodiments, the connection may include one or more disulfide bonds.

In some embodiments, the exterior member may be another CSQ2 dimer.

In some embodiments, the exterior member may be an electrical apparatus including a nano-gap.

In some embodiments, the in vitro electrical conductor is an ionic conductor.

In some embodiments, the ionic conductor may be configured to for conduction of cations.

In some embodiments, the cations may be calcium ions.

In some embodiments, the in vitro electrical conductor may be in a medium with a calcium ion concentration that facilitates CSQ2 protein dimerization.

According to another aspect of the present disclosure, an electrical device including the in vitro electrical conductor as described above is provided.

In some embodiments, the electrical device may further include a cation source or sink, including a composition capable of donating or accepting cations.

In some embodiments, the electrical device may further include an encasing structure which isolates the cation source or sink from the external environment.

In some embodiments, the electrical device may further include a gating electrode in contact with or in proximity to the biological tunnel structure, wherein the gating electrode is configured to apply sufficient electric field to induce electrical currents through the in vitro electrical conductor.

According to yet another aspect of the present disclosure, an ionic transistor is provided. The ionic transistor may include the in vitro electrical conductor described above.

According to still another aspect of the present disclosure, an in vitro method of conducting ions from an ion source to an ion sink is provided. The method may include providing an electrical conductor including a plurality of CSQ protein molecules and conducting ions through the electrical conductor to the ion sink. The CSQ protein molecules may be connected to form a tendril, a network structure, or a biological tunnel structure.

In some embodiments, the CSQ protein molecules may include CSQ1 molecules that use intermolecular interactions to form a tendril.

In some embodiments, the CSQ protein molecules may form a biological tunnel structure including a CSQ protein dimer. The CSQ protein dimer may include two CSQ molecules either of which is a CSQ1 molecule or a CSQ2 molecule.

In some embodiments, the CSQ protein dimer may include two CSQ1 molecules using an intermolecular interaction to form the biological tunnel structure.

In some embodiments, the CSQ protein dimer may include two CSQ2 molecules using an intermolecular interaction to form the biological tunnel structure.

In some embodiments, at least one of the CSQ2 protein molecules may include an amino acid sequence with at least 95% similarity to SEQ ID NO: 1, which consists of human CSQ2 protein sequence without amino acids 1-19.

In some embodiments, at least one of the CSQ2 protein molecules may consist of an amino acid sequence with at least 99% similarity to SEQ ID NO: 1, which consists of human CSQ2 protein sequence without amino acids 1-19.

In some embodiments, at least one of the CSQ2 protein molecules may include an amino acid sequence with at least 95% similarity to SEQ ID NO: 2, which consists of rat CSQ2 protein sequence without amino acids 1-19.

In some embodiments, at least one of the CSQ2 protein molecules may consist of an amino acid sequence with at least 99% similarity to SEQ ID NO: 2, which consists of rat CSQ2 protein sequence without amino acids 1-19.

In some embodiments, at least one of the CSQ2 protein molecules includes one or more amino acid mutations that enhance or reduce conductivity of the biological tunnel structure.

In some embodiments, at least one of the CSQ2 protein molecules includes a mutation of D (Asp) to N (Asn) at amino acid position 309 as defined in a full-length human or rat CSQ2 protein sequence.

In some embodiments, at least one of the CSQ2 protein molecules may include a D (Asp) to C (Cys) mutation, which may facilitate a connection between the biological tunnel structure to an exterior member.

In some embodiments, the D (Asp) to C (Cys) mutation may be at amino acid position 348 as defined in a full-length human or rat CSQ2 protein sequence.

In some embodiments, the connection may include one or more disulfide bonds.

In some embodiments, the exterior member may be another CSQ2 dimer.

In some embodiments, the exterior member may be an electrical apparatus including a nano-gap.

In some embodiments, the in vitro electrical conductor may be an ionic conductor.

In some embodiments, the ionic conductor may be configured for conduction of cations.

In some embodiments, the cations may be calcium ions.

In some embodiments, the in vitro electrical conductor may be in a medium with a calcium ion concentration that facilitates CSQ2 protein dimerization.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale.

These embodiments are non-limiting exemplary embodiments, in which like reference numerals represent similar structures throughout the several views of the drawings, and wherein.

DETAILED DESCRIPTION

Figure 1A:
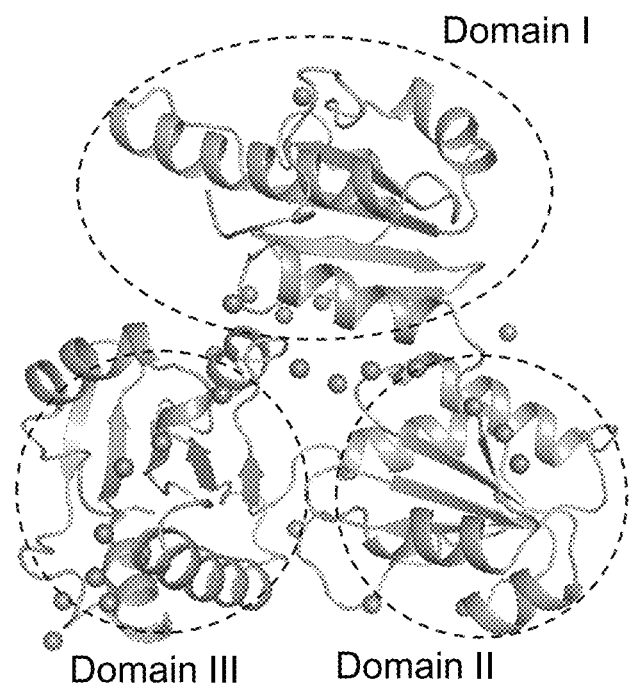
FIG. 1A is a schematic diagram illustrating an exemplary overall structure of human CSQ2 monomer complexed with calcium according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) is for the purpose of illustration and description only and are not intended to limit the scope of the present disclosure. It is understood that the drawings are not to scale.

According to an aspect of the present disclosure, an electrical conductor including a plurality of calsequestrin (CSQ) protein molecules is provided. In some embodiments, the plurality of CSQ protein molecules may be connected to form a tendril, a network structure, or a biological tunnel structure. The electrical conductor may be used in vitro or in vivo.

Figure 5A:
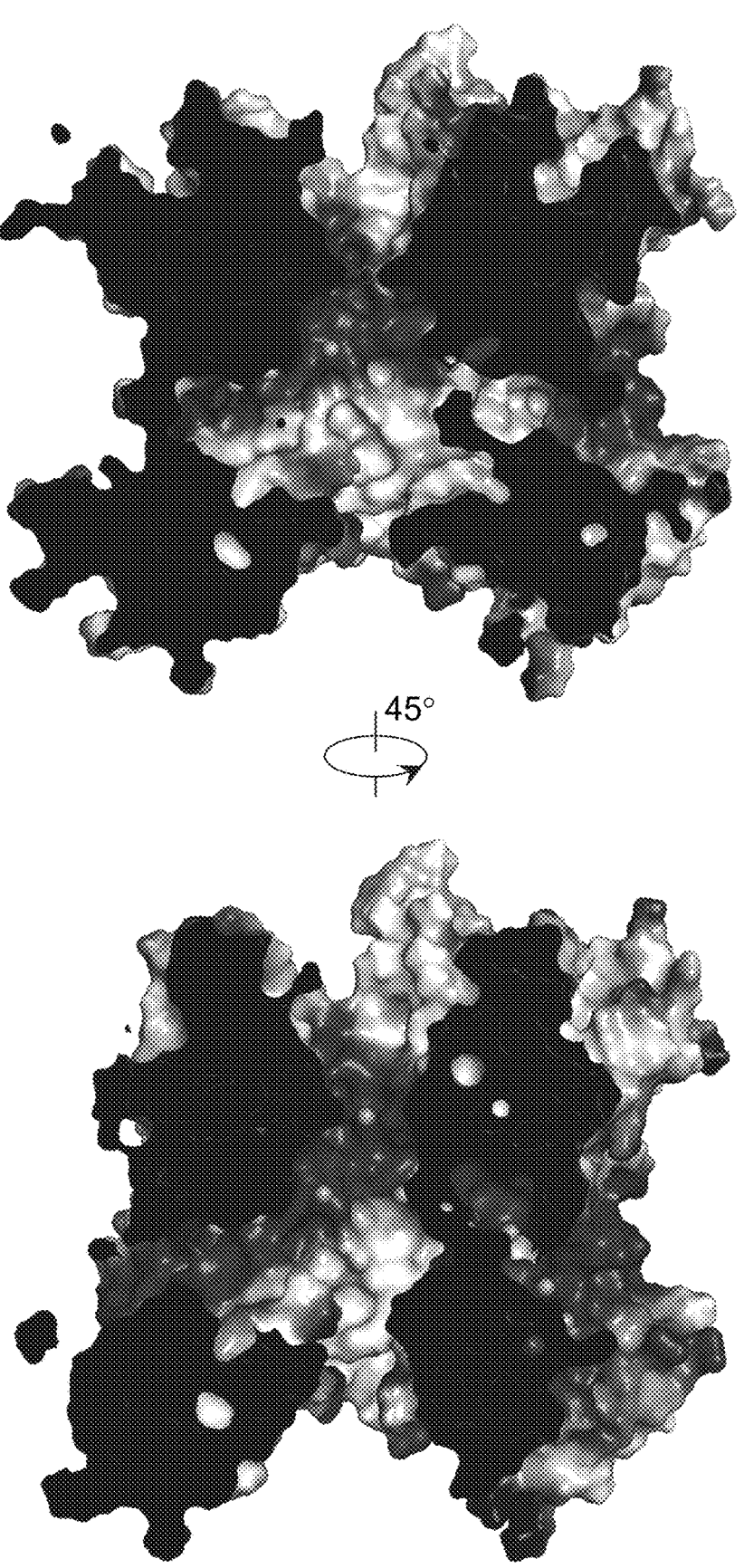
FIG. 5A is a schematic diagram illustrating cut-open views of the electrostatic potential for an exemplary human CSQ2 dimer according to some embodiments of the present disclosure.

In some embodiments, the electrical conductor may include a plurality of CSQ protein molecules that form a biological tunnel structure including a CSQ protein dimer. The CSQ protein dimer may include two CSQ molecules, either of which may be a CSQ1 molecule or a CSQ2 molecule. For example, a CSQ protein dimer may include two CSQ1 protein molecules. As another example, the CSQ protein dimer may include two CSQ2 protein molecules. As yet another example, the CSQ protein dimer may include a CSQ1 protein molecule and a CSQ2 protein molecule. FIG. 5A is a schematic diagram illustrating cut-open views of the electrostatic potential for an exemplary human CSQ2 protein dimer according to some embodiments of the present disclosure. As shown in FIG. 5A, the CSQ2 protein dimer includes a biological tunnel structure.

As used herein, the term "CSQ1 protein" refers to a wild type CSQ1 protein or a mutant type of the CSQ1 protein and refers to a full-length form, a mature form, an active fragment of the CSQ1 protein and/or a protein derived from the CSQ1 protein. Similarly, as used herein, the term "CSQ2 protein" refers to a wild type CSQ2 protein or a mutant type of the CSQ2 protein and refers to a full-length form, a mature form, an active fragment of the CSQ2 protein and/or a protein derived from the CSQ2 protein.

In some embodiments, two CSQ protein molecules may form the CSQ protein dimer in a face-to-face mode. Domain exchange may occur between the N-terminuses of the two CSQ molecules, which may facilitate the two CSQ protein molecules to form the CSQ protein dimer in the face-to-face mode.

In some embodiments, the electrical conductor may include the plurality of CSQ protein molecules that polymerize to form the tendril or the network structure. As used herein, the term "tendril" refers to a linear structure formed by a CSQ protein polymer. For instance, the tendril may be formed by a plurality of CSQ1 protein molecules (see e.g., T. Wagenknecht, C. E. Hsieh, B. K. Rath, S. Fleischer, M. Marko, Electron tomography of frozen-hydrated isolated triad junctions. *Biophys J* 83, 2491-2501 (2002) doi: 10.1016/S0006-3495(02)75260-0) or a plurality of CSQ2 protein molecules. As another example, the tendril or the network structure may be formed by a plurality of CSQ1 protein molecules and one or more CSQ2 protein molecules. As yet another example, the tendril or the network structure may be formed by a plurality of CSQ2 protein molecules and one or more CSQ1 protein molecules.

In some embodiments, the plurality of CSQ protein molecules may form the tendril or the network structure in a back-to-back mode and/or a side-by-side mode. For example, in the back-to-back mode, the helixes around the C-terminuses of the plurality of CSQ protein molecules (e.g., the plurality of CSQ1 protein molecules) may interact with each other, which may facilitate the plurality of CSQ protein molecules to form the tendril structure. As another example, in the side-by-side mode, the domain II and/or the domain III of a CSQ protein molecule (e.g., a CSQ2 protein molecule) may interact with the domain II and/or the domain III of other CSQ protein molecules. In some embodiments, the plurality of CSQ protein molecules may form the tendril and/or the network structure in both the back-to-back mode and the side-by-side mode, and/or other modes of intermolecular interactions.

Figure 6:
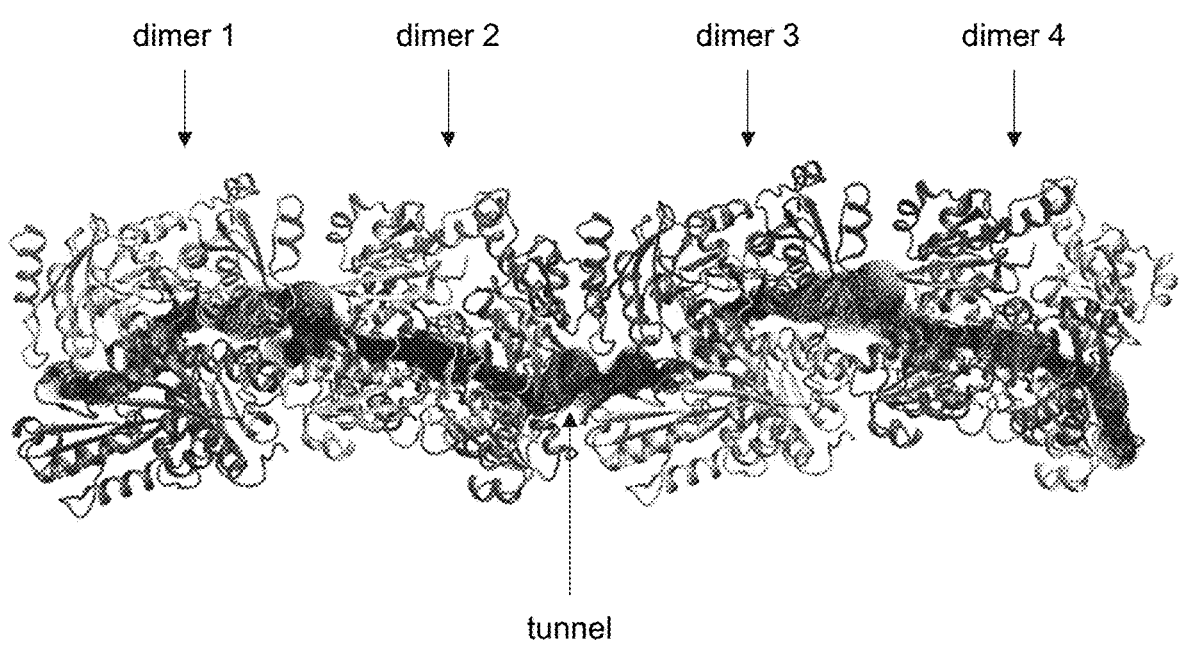
FIG. 6 is a schematic diagram illustrating an exemplary structure of a CSQ2 polymer formed by a plurality of CSQ2 dimers according to some embodiments of the present disclosure.

In some embodiments, a plurality of CSQ protein dimers may be connected to form a continuous biological tunnel structure. For example, a CSQ protein dimer may be connected with another CSQ protein dimer to form a tetramer. As another example, four CSQ protein dimers may be connected to form an octamer having the continuous biological tunnel structure as shown in FIG. 6. Positive ions such as $Ca^{2+}$ may be conducted through the continuous biological tunnel structure.

In some embodiments, the plurality of CSQ molecules may form the biological structure, the tendril, or the network structure using an intermolecular interaction. For instance, the intermolecular interaction may include a hydrogen bond, a salt bond, an electrostatic interaction, an ion-induced dipole force, a van der Waals force, a hydrophobic interaction, or the like, or any combination thereof. In some embodiments, the dimerization or polymerization of the plurality of CSQ molecules may be facilitated by the presence of cations, such as divalent ions. For example, a plurality of wild type CSQ protein molecules and/or a plurality of CSQ protein mutant molecules may form the biological structure, the tendril, or the network structure under the presence of $Ca^{2+}$, $Mg^{2+}$, $Zn^{2+}$, $Fe^{2+}$, $Cu^{2+}$, or the like, or any combination thereof. In some embodiments, the cations may be conducted through the biological tunnel structure, the tendril, or the network structure, which may enable the electrical conductor including the plurality of CSQ protein molecules to be conductive.

The CSQ protein molecules are capable of cyclically binding and releasing cations. For example, the CSQ protein molecules can bind and release calcium ions ($Ca^{2+}$) in a cycle of excitation-contraction coupling of muscles. The CSQ protein molecule is rich in acidic residues (e.g., acidic residues of aspartic acid and glutamic acid) at the protein surface, which may serve as the $Ca^{2+}$ binding ligands.

In some embodiments, two CSQ monomers may form a dimer. A plurality of amino acid residues (e.g., acid residues) of the CSQ protein dimer may form a biological tunnel structure on the protein surface (as will be described in Example 1). $Ca^{2+}$ may be conducted through the biological tunnel structure. Similarly, $Ca^{2+}$ may be conducted through the tendril or the network structure of a CSQ protein polymer.

In some embodiments, the plurality of CSQ protein molecules may be connected through covalent bonds to form the biological structure, the tendril, or the network structure. For example, a crosslinking agent may be used to connect a plurality of CSQ protein molecules by reacting with a plurality of amino acid residues of the plurality of CSQ protein polymers. Exemplary crosslinking agents may include but not limited to 3-maleimidopropionic acid, dithio-bis-succinimidyl propionate, succinimidyl-p-formyl-benzoate, disuccinimidyl sebacate, biotin hydrazide, or the like, or any combination thereof.

In some embodiments, the CSQ protein molecules in the electrical conductor may be human CSQ protein molecules, rat CSQ protein molecules, chicken CSQ protein molecules, dog CSQ protein molecules, zebrafish CSQ protein molecules, rabbit CSQ protein molecules, cattle CSQ protein molecules, giant panda CSQ protein molecules, pig CSQ protein molecules, or the like, or any combination thereof.

In some embodiments, at least one of the CSQ2 protein molecules in the electrical conductor may include an amino acid sequence with at least 95%, 96%, 97%, 98%, or 99% similarity to SEQ ID NO: 1, which consists of human CSQ2 protein sequence without amino acids 1-19. The amino acids 1-19 form the signal peptide of the human CSQ2 protein molecule. In some embodiments, at least one of the CSQ2 protein molecules in the electrical conductor may include an amino acid sequence with at least 70%, 75%, 78%, 80%, 81%, 82%, 83%, 84%, 85%, 86%, 87%, 88%, 89%, 90%, 91%, 92%, 93%, or 94% similarity to SEQ ID NO: 1.

In some embodiments, at least one of the CSQ2 protein molecules in the electrical conductor may include an amino acid sequence with at least 95%, 96%, 97%, 98%, or 99% similarity to SEQ ID NO: 2, which consists of rat CSQ2 protein sequence without amino acids 1-19. The amino acids 1-19 form the signal peptide of the rat CSQ2 protein molecule. In some embodiments, at least one of the CSQ2 protein molecules in the electrical conductor may include an amino acid sequence with at least 70%, 75%, 78%, 80%, 81%, 82%, 83%, 84%, 85%, 86%, 87%, 88%, 89%, 90%, 91%, 92%, 93%, or 94% similarity to SEQ ID NO: 2.

In some embodiments, the conductivity of the electrical conductor may be modulated by changing the count of the CSQ protein molecules included in the electrical conductor. In some embodiments, the conductivity of the electrical conductor may be modulated by changing the way in which the CSQ protein molecules are organized. For instance, the electrical conductor may include a plurality of CSQ protein polymers that are connected in series. As another example, the electrical conductor may include a plurality of CSQ protein polymers that are connected in parallel. In some embodiments, the conductivity of the electrical conductor may be modulated by causing at least a portion of the CSQ protein molecules in the electrical conductor to polymerize or depolymerize. For example, the electrical conductor may include a medium including positive ions that may affect the polymerization and/or depolymerization of the CSQ protein molecules in the electrical conductor. The positive ions may include $Ca^{2+}$, $Mg^{2+}$, $Zn^{2+}$, $Fe^{2+}$, $Cu^{2+}$, or the like, or any combination thereof. The conductivity of the electrical conductor may be modulated by changing the concentration of the positive ions. As another example, the conductivity of the electrical conductor may be changed by adding an agent that may cause the at least a portion of the CSQ protein molecules in the electrical conductor to polymerize or depolymerize.

In some embodiments, at least one of the CSQ protein molecules in the electrical conductor may include one or more amino acid mutations that enhance or reduce conductivity of the biological tunnel structure. For example, one or more amino acids of the at least one of the CSQ protein molecules may be replaced with one or more different amino acids (e.g., replaced with the aspartic acid and/or the glutamic acid). As another example, one or more amino acids may be inserted to the at least one of the CSQ protein molecules. As yet another example, one or more amino acids of the at least one of the CSQ protein molecules may be deleted. Merely by way of example, at least one of the CSQ2 protein molecules in the electrical conductor may include a mutation of D (aspartic acid, briefly referred to as "Asp") to N (asparagine, briefly referred to as "Asn") at amino acid position 309 as defined in a full-length human or rat CSQ2 protein sequence, which may decrease the conductivity of the biological tunnel structure (as will be described in Example 4). In some embodiments, the one or more amino acid mutations may be accomplished by mutating the nucleic acid that encodes the CSQ protein using genetic engineering techniques, for example, a site-directed mutagenesis technique, a random mutation technique, etc.

In some embodiments, the plurality of CSQ2 protein molecules that form the biological tunnel structure, the tendril, or the network structure may be connected to an exterior member. In some embodiments, the exterior member may be another CSQ2 protein dimer or polymer. In some embodiments, the exterior member may be an electrical device or a part thereof. For instance, the plurality of CSQ2 protein molecules that form the biological tunnel structure, the tendril, or the network structure may be connected to or immobilized in a nano-gap or a micro-gap of the electrical device. In some embodiments, the connection of the plurality of CSQ2 protein molecules to the exterior member may be accomplished through one or more disulfide bonds, peptide bonds, ester bonds, or the like, or any combination thereof.

In some embodiments, at least one of the CSQ2 protein molecules in the electrical conductor may include a mutation which facilities the connection of the biological tunnel structure, the tendril, or the network structure to the exterior member. For instance, the mutation may include a D (Asp) to C (cysteine, briefly referred to as "Cys") mutation. Merely by way of example, the D (Asp) to C (Cys) mutation may occur at amino acid position 348 as defined in a full-length human or rat CSQ2 protein sequence (as will be described in Example 3).

In some embodiments, the electrical conductor may be an ionic conductor. The ionic conductor may be configured to conduct positive ions. For instance, the ionic conductor may be configured to conduct cations, such as $Ca^{2+}$, $Mg^{2+}$, $Zn^{2+}$, $Fe^{2+}$, $Cu^{2+}$, or the like, or any combination thereof. In some embodiments, the ionic conductor may be configured to conduct the positive ions from an ion source to an ion sink. The ion source may include a composition capable of donating ions. The ion sink may include a composition capable of accepting ions. Merely by way of example, two portions on both ends of the ionic conductor may be immersed in a first medium and a second medium containing $Ca^{2+}$, respectively. The ionic conductor may be configured to conduct the $Ca^{2+}$ transfer between the first medium and the second medium.

In some embodiments, the electrical conductor may be deployed in a medium with a $Ca^{2+}$ concentration that facilitates CSQ protein dimerization and/or polymerization. For instance, the $Ca^{2+}$ concentration that facilitates CSQ2 protein dimerization may be 1 μmol/L to 1 mmol/L, or the like. The plurality of CSQ2 protein molecules in the electrical conductor may form one or more dimers or polymers when the electrical conductor is deployed in the medium. In some embodiments, the conductivity of the electrical conductor may be modulated by changing the $Ca^{2+}$ concentration in the medium. For instance, the $Ca^{2+}$ concentration may be changed from a value that facilitates the CSQ protein dimerization and/or polymerization into a value that facilitates the CSQ protein dedimerization and/or depolymerization.

In some embodiments, the electrical conductor that include the plurality of CSQ protein molecules may be fabricated in various shapes and sizes. For example, the electrical conductor may be a sphere, a semi-sphere, a cylinder, a cube, a loop, a tube, an inclined prism, a tetrahedron, a pentahedron, a hexahedron, an irregular shape, etc. In some embodiments, the length of the electrical conductor may be 6 nanometers (nm), 12 nm, 24 nm, 240 nm, 3 μm, 30 μm, 300 μm, 600 μm, 3 mm, 12 mm, or the like. In some embodiments, the diameter or width of the electrical conductor may be 6 nm, 12 nm, 24 nm, 240 nm, 3 μm, 30 μm, 300 μm, 600 μm, 3 mm, 12 mm, or the like.

In some embodiments, the electrical conductor may be a nanowire including one or more tendrils formed by the plurality of CSQ protein molecules. The nanowire may be configured for connecting an electrical conductor with another electrical conductor.

In some embodiments, the electrical conductor may include one or more layers of films (also referred to as one or more "CSQ protein films") which include the plurality of CSQ protein molecules. In some embodiments, the electrical conductor may further include a substrate made of materials such as metal, glass, plastics, ceramics, alloy, or the like, or any combination thereof. The one or more layers of CSQ protein films may be formed on the substrate using a film formation technique.

The film formation technique may include but not limited to drop casting, spin casting, blading, spraying, printing, electronic spinning, or the like, or any combination thereof. As another example, the one or more layers of CSQ protein films may be fabricated alone and then be adhered to the substrate using an adhesion agent. The adhesion agent may be configured to enhance the bonding of the one or more CSQ protein films to the substrate by interactions such as covalent forces, ionic forces, electrostatic forces, or the like, or any combination thereof.

According to another aspect of the present disclosure, an electrical device is provided. The electrical device may include the electrical conductor including the plurality of CSQ protein molecules that form the biological tunnel structure, the tendril, or the network structure.

In some embodiments, the electrical device may be fabricated in a micrometer-scale size or a nanometer-scale size. The electrical device may be used in vitro or in vivo. For instance, the electrical device may be used in a biological system. Merely by way of example, the biological system may include a cell (e.g., a myocyte), a tissue (e.g., a tumor), an organ (e.g., a kidney or a liver), a living body (e.g., an animal body or a human body), etc. In some embodiments, the electrical device used in the biological system may be configured to identify and destroy cancer cells, eliminate the thrombus formed in blood vessels, kill parasites, remove kidney stones, deliver a drug to a target position, or the like, or any combination thereof. In some embodiments, the electrical device may be used in vitro for manipulating molecules and/or atoms.

In some embodiments, the electrical device may include a cation source and/or a cation sink. The cation source may include a composition capable of donating cations. Merely by way of example, the composition capable of donating cations may include a gas, a liquid, or a solid containing divalent ions, such as $Ca^{2+}$ For instance, the ion source may include a solution containing $Ca^{2+}$. The cation sink may include a composition capable of accepting cations. For instance, the composition capable of accepting cations may include a gas, a liquid, or a solid containing a plurality of acid groups or negative charges. In some embodiments, the electrical device may be configured to sense or introduce a positive ion flux, such as a $Ca^{2+}$ flux. For instance, the electrical device may be used in cardiomyocytes to determine if there is a disorder in $Ca^{2+}$ modulation in the cardiomyocytes and/or cardiac excitation-contraction coupling of the cardiac muscles. As another example, the electrical device may be used to treat a disorder in $Ca^{2+}$ modulation in the cardiomyocytes and/or cardiac excitation-contraction coupling of the cardiac muscles.

In some embodiments, the electrical device may include a gating electrode in contact with or in proximity to the biological tunnel structure, the tendril, or the network structure. The gating electrode may be configured to apply a sufficient electric field to induce electrical currents through the electrical conductor. The gating electrode may be made of a conductive material, such as metal (e.g., gold, silver, lithium), alloy (e.g., copper alloy, aluminum alloy), metal oxide, graphene, conductive fiber, or the like, or any combination thereof. In some embodiments, the magnitude of the electrical currents and/or the capability of conducting the positive ions of the electrical device may be modulated by changing the strength of the electrical field applied to the electrical device.

In some embodiments, the electrical device may include an encasing structure which isolates the cation source or sink from the external environment. For instance, the encasing structure may be made of a non-conductive material, such as glass, porcelain, plastics, rubber, or the like, or any combination thereof. The encasing structure may also be configured to protect the cation source and/or the cation sink.

According to yet another aspect of the present disclosure, an ionic transistor is provided. The ionic transistor may include the electrical conductor including the plurality of CSQ protein molecules that form the biological tunnel structure, the tendril, or the network structure. In some embodiments, the ionic transistor may further include an ion source, an ion sink, and a gate electrode which can apply a positive or a negative electric field to the biological tunnel structure, the tendril, or the network structure formed by the plurality of CSQ protein molecules.

In some embodiments, the ionic transistor may be implemented in various forms, for example, as a switch and/or an amplifier. The switch may be configured to start to allow an ion current to flow through the ionic transistor, or stop the ion current flowing through the ionic transistor. The amplifier may be configured to amplify a current and/or electrical signals.

According to still another aspect of the present disclosure, a method of conducting ions from an ion source to an ion sink is provided. The method may include providing an electrical conductor including a plurality of CSQ protein molecules that are connected to form a tendril, a network structure, or a biological tunnel structure. The method may further include conducting ions from the ion source to the ion sink through the electrical conductor. An electric field may be applied to the electrical conductor to facilitate the conduction of the ions. In some embodiments, the ion conductivity of the electrical conductor may be modulated by changing the strength of the electric field, the count of CSQ protein molecules, the way in which the CSQ protein molecules are organized, the concentration of positive ions (e.g., $Ca^{2+}$, $Mg^{2+}$, $Zn^{2+}$, $Fe^{2+}$, and/or $Cu^{2+}$), or the like, or any combination thereof. Details regarding the electrical conductor may be found elsewhere in the present disclosure and are not repeated here.

The present disclosure is further described according to the following examples, which should not be construed as limiting the scope of the present disclosure.

EXAMPLES

Methods

Cloning, Expression, and Purification of CSQ2

RNA isolation was performed using the left-ventricle of rats using the RNeasy mini kit according to the instructions of the manufacturer (QIAGEN). Total RNA was transcribed using the SuperScript kit (Thermo Fisher) and was used for full length CSQ2 amplification. The cDNA that encodes amino acids 20-413 of rat CSQ2 (without the signal peptide) was amplified and introduced into a pET-28a vector (Novagen) with an N-terminal His-tag.

The cDNA without the sequence encoding amino acids 1-19 (which forms the signal peptide) of human CSQ2 was synthesized and subcloned into a pET-28a vector. Mutation was introduced by a site-directed mutagenesis protocol using the plasmid containing wild-type human CSQ2 without the signal peptide.

Overexpression and purification of CSQ2 were performed. E. coli (DE3 Rosetta) was transfected with a constructed plasmid and cultured at 37° C. until optical density (OD) measured at 600 nm reached 0.6. Protein expression was induced with addition of 0.5 mM isopropyl β-D-thiogalactoside (IPTG) and the culture was continued for 20 hours at 18° C. Cell pellets harvested by centrifugation was re-suspended and sonicated on ice in a buffer A. The buffer A contained (in mM) 20 Tris-HCl pH 7.5, 500 NaCl. The expressed protein was purified using $Ni^{2+}$-affinity chromatography (HisTrap HP, GE Healthcare), ion-exchange chromatography (HiTrap Q FF, GE Healthcare) and size-exclusion chromatography (HiLoad 16/600 superdex 200, GE Healthcare) at room temperature. The elution buffer for $Ni^{2+}$-affinity chromatography was buffer A supplemented with 500 mM imidazole. The eluted protein was diluted five times using buffer Q (20 mM Tris-HCl pH 7.5, 5% glycerol)

and loaded to a HiTrap Q FF column. The protein was eluted with gradient buffer A elution, pooled and digested using the thrombin (GE Healthcare) to remove His-tag before size-exclusion chromatography in which the elution buffer differs among samples used for different assays. For crystallization, the elution buffer was the buffer A. For conductance measurement using a nanogapped graphene device, the protein in the dimer form was eluted with a buffer S (20 mM Tris-HCl pH 7.5, 300 mM KCl) supplemented with 1 mM CaCl$_2$. For other assays (multi-angle light scattering, analytical ultracentrifugation, and turbidity assay), buffer S was used. Purified protein was concentrated to 50 mg/ml using a 10 kilo Dalton (kDa) concentrator (Amicon Ultra, Millipore). The concentrated protein was then aliquoted, flash frozen and stored at –80° C. before use.

Crystallization, Data Collection, and Structure Determination

Human CSQ2 crystals were obtained according to a hanging drop vapor diffusion method (24-well hanging drop plate, XtalQuest) at 16° C. using 1.5 μL protein solution (25 mg/ml) and 1.5 μL reservoir solution containing 100 mM Na cacodylate (pH 6.0), 25% (vol/vol) 2-methyl-2,4-pentanedio (MPD) and 40 mM calcium lactate. Small needle-like crystals appeared within two days. After several rounds of stick seeding, the crystals had grown to approximately 50×50× 400 μm. The Se-Met CSQ2 crystals were obtained using the same process. Diffraction data of native and Se-Met crystals were collected and were processed using CCP4 program suit (see, e.g., Winn, M. D. et al. Overview of the CCP4 suite and current developments. Acta. Crystallogr. D. Biol. Crystallogr. 67, 235-242 (2011). doi: 10.1107/ S0907444910045749). The initial phase was determined by MR-SAD using PHENIX (see, e.g., P. D. Adams et al., PHENIX: a comprehensive Python-based system for macromolecular structure solution. Acta. Crystallogr. D. Biol. Crystallogr. 66, 213-221 (2010). doi: 10.1107/ S0907444909052925). The model building was performed using PHENIX. The model was manually improved by Coot (see, e.g., P. Emsley et al., Features and development of Coot. Acta. Crystallogr. D. Biol. Crystallogr. 66, 486-501 (2010). doi: 10.1107/S0907444910007493) and refined by PHENIX. Rat CSQ2 crystals were obtained using the same procedure as the human crystals, except the reservoir solution contains 200 mM MES pH6.5, 26% PEG3000, 200 mM (C$_3$H$_5$O$_2$)$_2$Ca. The phase was determined by molecular replacement using human CSQ2 structure as a searching model. The atomic model was manually built by Coot and refined by PHENIX. The statistics of data collection, phasing and refinement are listed in Table 1 (shown in Example 1).

Nanogapped Graphene Device Fabrication and Characterization

Devices with nanogapped graphene point contact arrays were fabricated by a new dash-line lithographic (DLL) method (see, e.g., P. D. Adams et al., PHENIX: a comprehensive Python-based system for macromolecular structure solution. Acta. Crystallogr. D. Biol. Crystallogr. 66, 213-221 (2010). doi: 10.1107/S0907444909052925).

Carboxylic acid activation: n-hydroxy succinimide (NHS) was first dissolved in dry pyridine at a concentration of about 10$^{-2}$ M to obtain an NHS solution. Then the graphene devices and 1-Ethyl-3-(3-dimethylaminopropyl)carbodiimide (EDCI), a well-known carbodiimide dehydrating/activating agent, were added to the NHS solution for forming carboxyl active ester, for one day in the dark. Thereafter, the devices were taken out from the NHS solution, washed with copious chloroform, and dried in a nitrogen (N$_2$) gas stream to obtain carboxylic acid activated graphene devices.

Linker formation: the carboxylic acid activated graphene devices were immersed in a chloroform solution containing 6 mM poly(N,N-diethylacrylamide) (PDEA) and 20 mM N,N-Diisopropylethylamine (DIPEA) for one day in the dark. The devices were taken out from the chloroform solution, washed with copious chloroform, and dried in a N$_2$ gas stream subsequently.

Graphene electrode protection: triton X-100 polymer coatings were used to prevent nonspecific binding of proteins on the carbon electrode surfaces (See e.g., M. Shim, N. W. Shi Kam, R. J. Chen, Y Li, H. Dai, Functionalization of Carbon Nanotubes for Biocompatibility and Biomolecular Recognition. Nano letters 2, 285-288 (2002) doi: 10.1021/ n1015692j). 0.1 wt % Triton X-100 aqueous solution was dropped on the device surface for 4 h. Then the device surface was rinsed by deionized water and dried in a N$_2$ gas stream.

Protein Immobilization on Nanogapped Graphene Device and Data Collection

The as-formed devices were immersed in the CSQ2 protein solution (1 mg/ml) in the storage buffer for 4 h at 4° C. to connect the CSQ2 dimer into the single-molecule junctions (SMJs). After 4 h, the protein solution was removed. The nanogapped graphene devices were rinsed and stored in a test buffer. The test buffer contained 20 mM 4-(2-hydroxyethyl)-1-piperazineethanesulfonic acid (HEPES), 125 mM KCl and 1 mM CaCl$_2$)), and the pH of the test buffer was 7.2.

The conductance of the resultant naogapped graphene device connected with the CSQ2 protein dimer and an original naogapped graphene device was measured using an Agilent 4155C semiconductor characterization system and a Karl Suss (PM5) manual probe station in the ambient atmosphere.

Multi-Angle Light Scattering

The protein molecular weight was determined using size-exclusion chromatography followed by multi-angle light scattering. The CSQ2 wild-type or CSQ2$^{D309N}$ mutant protein (100 μl, 1 mg/ml) was loaded to a Superdex 200 10/300 GL column (GE Healthcare) and eluted with an elution buffer (20 mM Tris-HCl pH 7.5, 300 mM KCl, 0.03% NaN$_3$, with or without 1 mM CaCl$_2$)) at a flow rate of 0.5 ml/min. Protein elute was passed in an ultraviolet (UV) detector of ATKA pure chromatography system (GE Healthcare) and a multi-angle laser light scattering detector (MiniDawn, Wyatt Tech). The multi-angle light scattering experiments were performed at room temperature. The scattering data were collected and analyzed using the ASTRA 6.1 software provided with the multi-angle laser light scattering detector. The relative weight-averaged molecular mass was determined using the Zimm fitting model for data analysis and estimated using an extrapolation of a Zimm plot to zero angle.

Turbidity Assay

The CSQ2 protein was diluted to 0.5 mg/ml in the assay buffer (pH 7.5, 20 mM HEPES, 150 mM KCl). Calcium stock solution containing 0 mM, 6 mM, 20 mM, 60 mM, and 200 mM was added to the CSQ2 protein solution, respectively, in a 96-well clear plate to cause the final calcium concentrations of the mixture to be 0 mM, 0.3 mM, 1 mM, 3 mM, and 10 mM, respectively, with 3 repeats for each concentration. After 2 minutes of shaking, the absorbance at 350 nm was measured with BioTek Cytation5 (BioTek). These procedures were performed at room temperature.

Example 1 Calcium Ions Bound at the Dimer Interface of CSQ2 in a Consecutive Manner The crystal structures of the human CSQ2 protein and the rat CSQ2 protein were determined to be 2.2 Å and 2.8 Å with a high concentration of $Ca^{2+}$ in the reservoir solution (40 mM $Ca^{2+}$ for human CSQ2, 200 mM $Ca^{2+}$ for rat CSQ2). In one asymmetry unit of human CSQ2 crystal, four monomers were identified, while ten monomers were identified for rat CSQ2 crystal.

minal region of the CSQ2 monomer are shown, and the calcium ions are illustrated as colored spheres. Analysis of all the positions of $Ca^{2+}$ reveals that up to 34 $Ca^{2+}$ ions can bind to one CSQ2 monomer. The number of bound $Ca^{2+}$ ions identified in our structure agrees with the $Ca^{2+}$ binding capacity reported earlier.

Figure 2A:
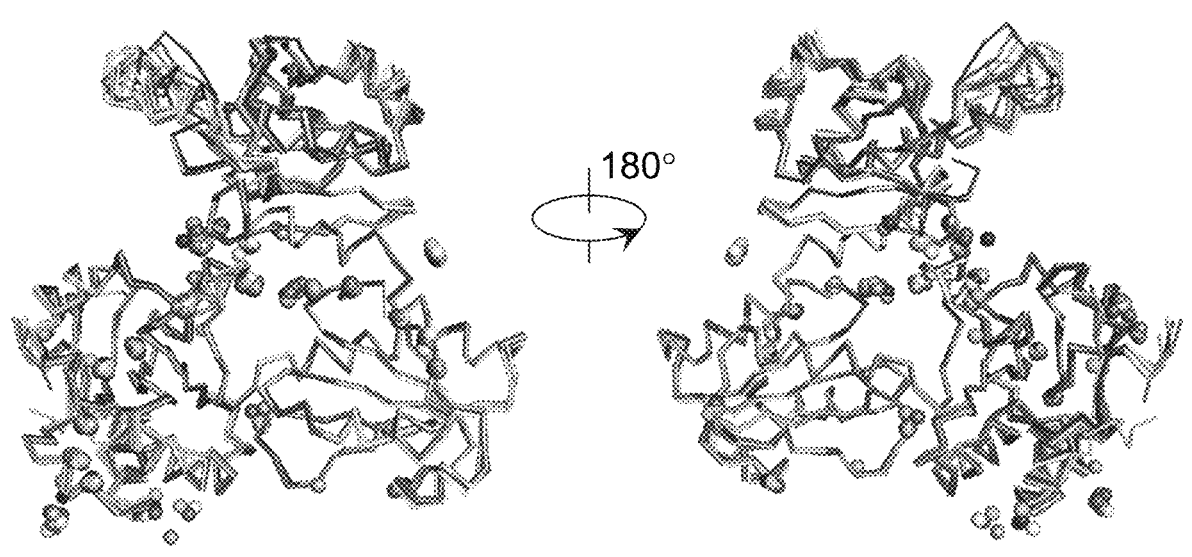
FIG. 2A is a schematic diagram illustrating a comparison of exemplary structures of superimposed seven dimers from human and rat $Ca^{2+}$ bound CSQ2 structures according to some embodiments of the present disclosure.
Figure 2B:
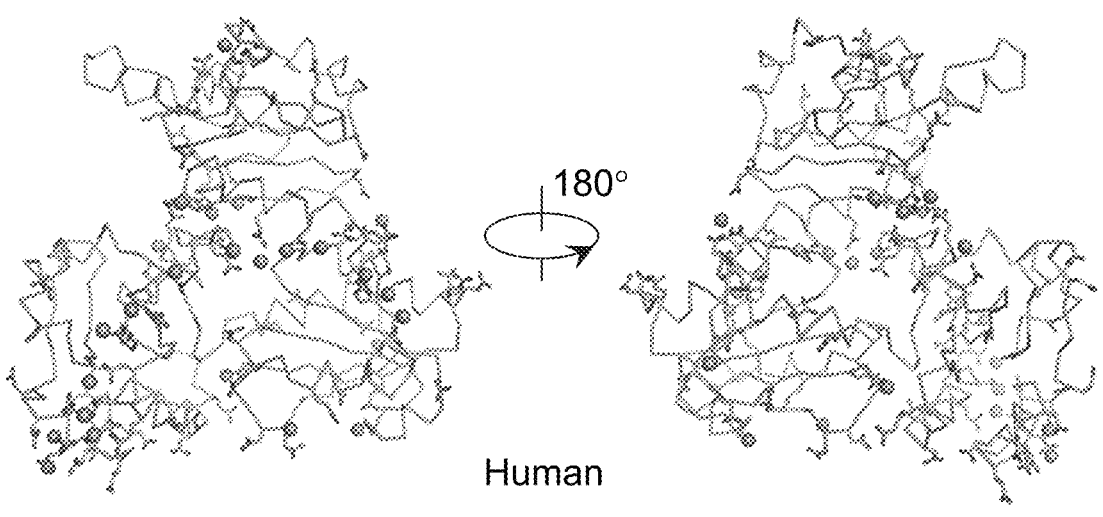
FIG. 2B is a schematic diagram illustrating an exemplary distribution of negatively charged residues on a human CSQ2 monomer according to some embodiments of the present disclosure.
Figure 2C:
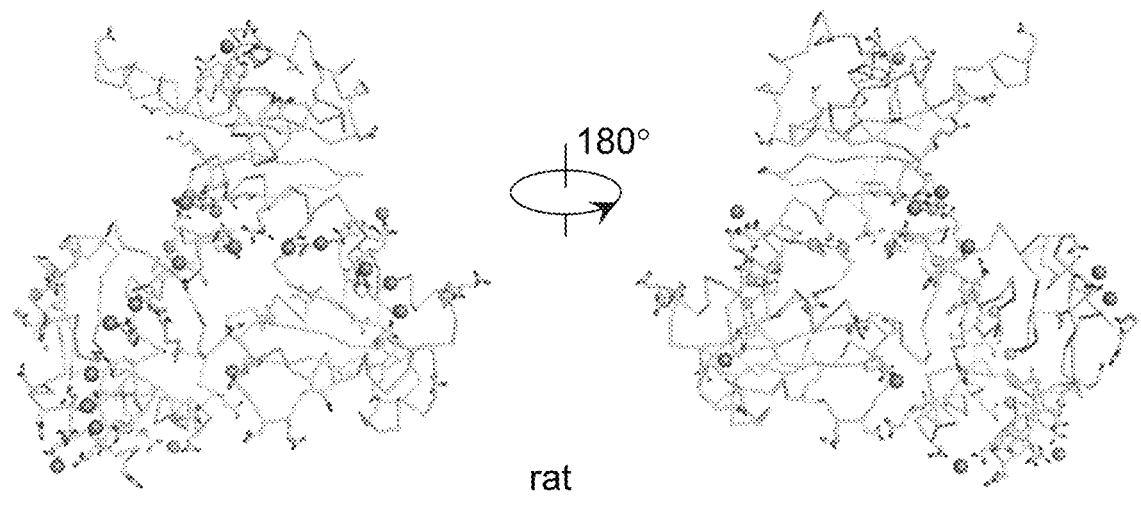
FIG. 2C is a schematic diagram illustrating the distribution of negatively charged residues on an exemplary rat CSQ2 monomer according to some embodiments of the present disclosure.

FIG. 2B is a schematic diagram illustrating an exemplary distribution of negatively charged residues on a human CSQ2 monomer according to some embodiments of the present disclosure. FIG. 2C is a schematic diagram illustrating the distribution of negatively charged residues on an exemplary rat CSQ2 monomer according to some embodiments of the present disclosure. As can be seen from FIG. 2B

TABLE 1

| Statistics of data collection and refinement of CSQ2 | | | |
| --- | --- | --- | --- |
| | human CSQ2 | Se-Met human CSQ2 | rat CSQ2 |
| Data collection | | | |
| Space group | I2 | I2 | P21 |
| Cell dimensions | | | |
| a, b, c (Å) | 157.57, 68.39, 157.57 | 157.17, 68.22, 157.17 | 137.85, 76.36, 218.19 |
| $\alpha, \beta, \gamma$ (°) | 90.00, 91.49, 90.00 | 90.00, 91.22, 90.00 | 90.00, 105.69, 90.00 |
| Resolution (Å) | 39.38-2.30 (2.35-2.30)$^a$ | 78.75-2.50 (2.64-2.50) | 25.00-2.80 (3.00-2.80) |
| $R_{sym}$ or $R_{merge}$ (%) | 11.0 (54.7) | 14.4 (49.5) | 19.7 (75.4) |
| Average I/σ(I) | 16.9 (5.3) | 14.2 (6.6) | 7.34 (2.83) |
| Completeness (%) | 100.0 (100.0) | 99.5 (99.4) | 45.5 (99.7) |
| Redundancy | 12.5 (12.5) | 10.7 (10.7) | 3.7 (3.8) |
| Refinement | | | |
| Resolution (Å) | 20.00-2.3 | | 20.00-2.8 |
| No. reflections | 74946 | | 108956 |
| $R_{wrok}/R_{free}$ | 0.208/0.234 | | 0.214/0.260 |
| No. atoms | | | |
| Protein | 11367 | | 28604 |
| Ligand/ion | 75 | | 172 |
| Water | 978 | | 506 |
| B-factors | | | |
| Protein | 35.5 | | 47.3 |
| Ligand/ion | 50.6 | | 52.2 |
| Water | 38.8 | | 39.8 |
| R.m.s. deviations | | | |
| Bond lengths (Å) | 0.006 | | 0.01 |
| Bond angles (°) | 0.827 | | 1.24 |
| Ramachandran statistics | | | |
| Favored regions (%) | 97.47 | | 93.78 |
| Allowed regions (%) | 2.53 | | 5.56 |
| Outliers (%) | 0 | | 0.66 |

For each structure one crystal was used.
$^a$Values for the highest resolution shell are shown in parentheses.

Figure 1B:
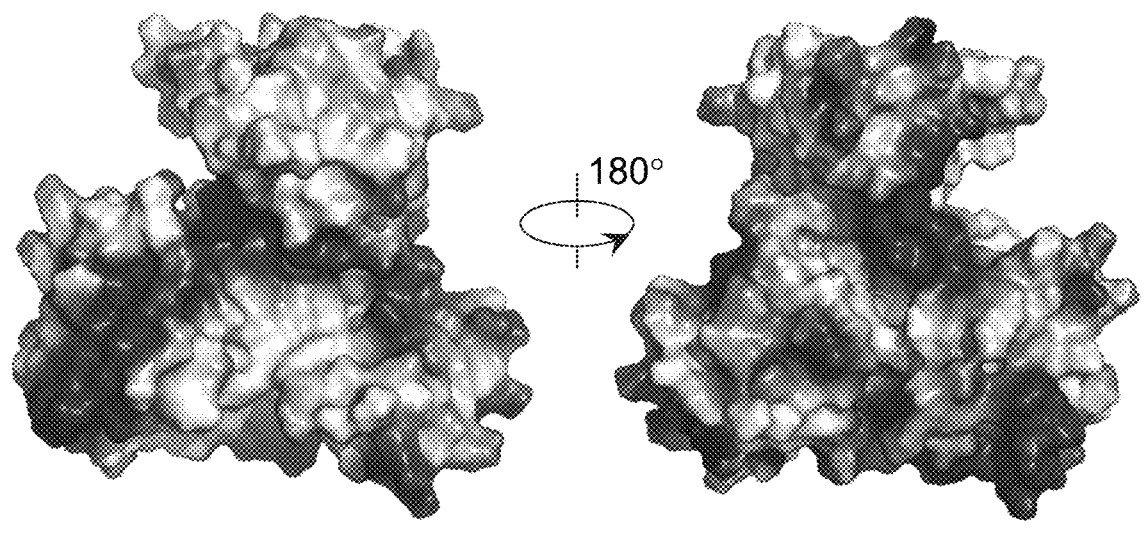
FIG. 1B is a schematic diagram illustrating an electrostatic potential surface of an exemplary CSQ2 monomer according to some embodiments of the present disclosure.
Figure 1C:
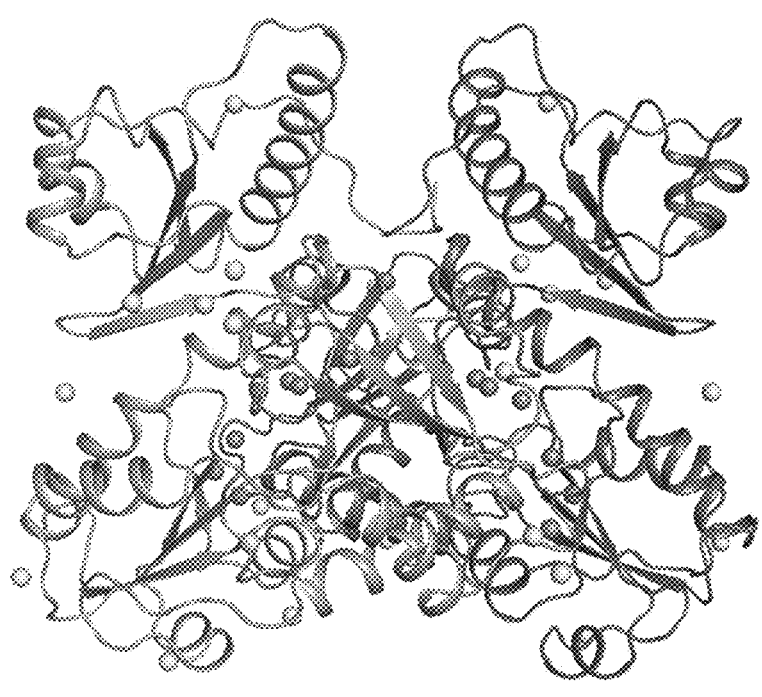
FIG. 1C is a schematic diagram illustrating an exemplary structure of human CSQ2 dimer according to some embodiments of the present disclosure.
Figure 1D:
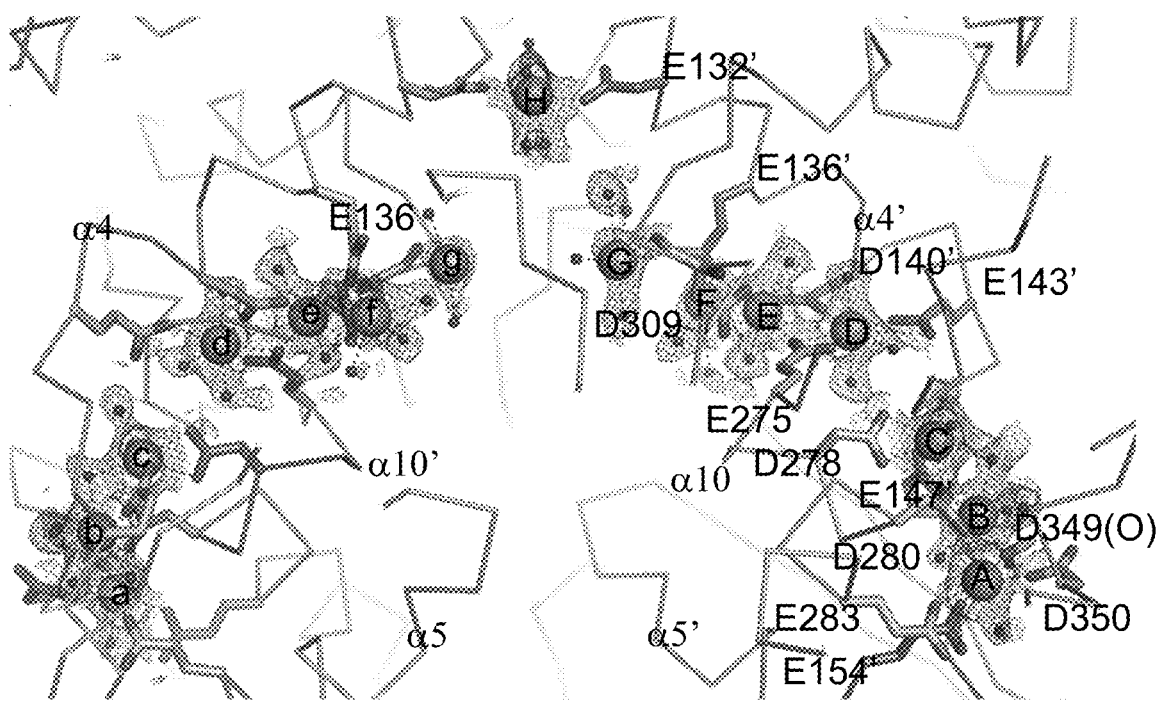
FIG. 1D and FIG. 1E are schematic diagrams illustrating exemplary calcium ions bond at the human CSQ2 dimer interface according to some embodiments of the present disclosure.
Figure 1E:
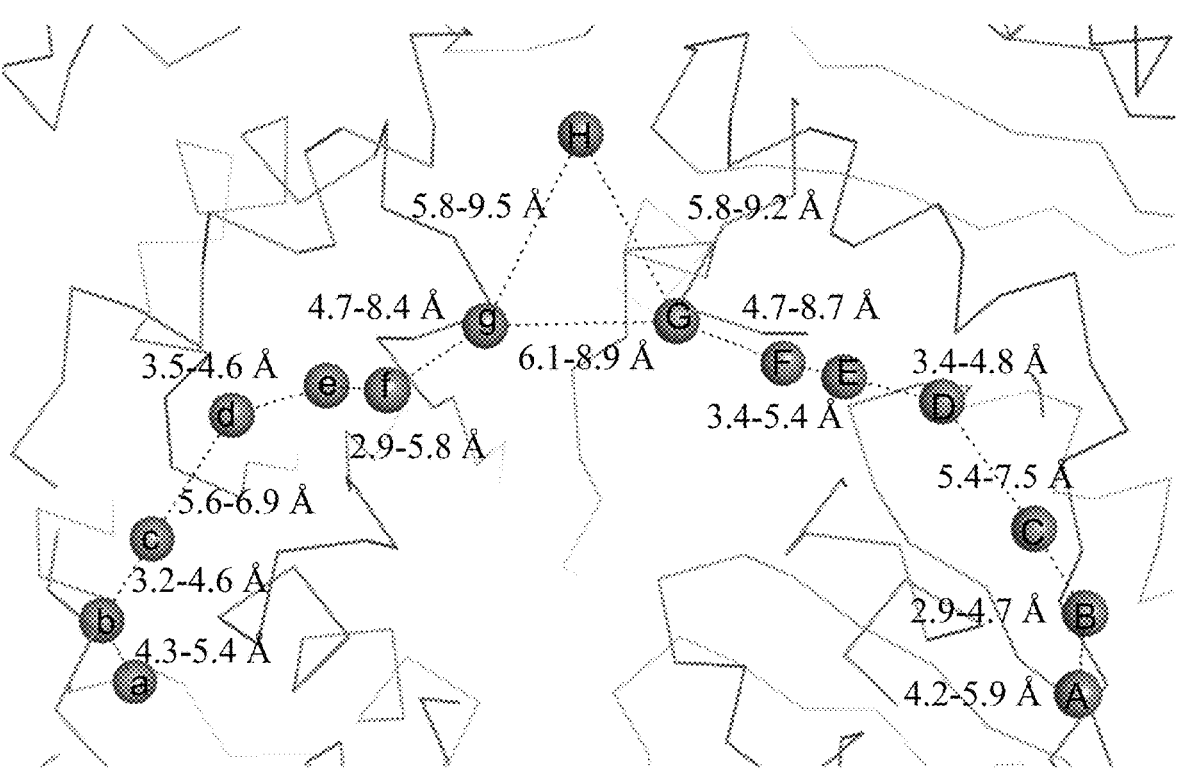
Figure 1F:
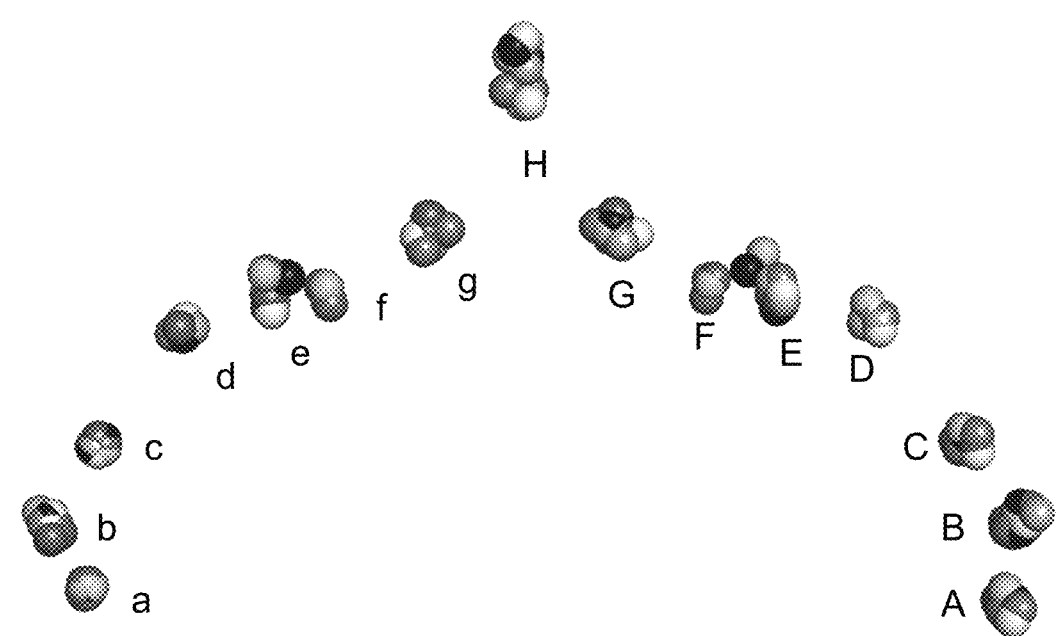
FIG. 1F and FIG. 1G are schematic diagrams illustrating a comparison of exemplary structures of the domain II of 2 dimers from human CSQ2, 5 dimers from rat CSQ2 structure and their C2-symmetry related dimers according to some embodiments of the present disclosure.
Figure 1G:
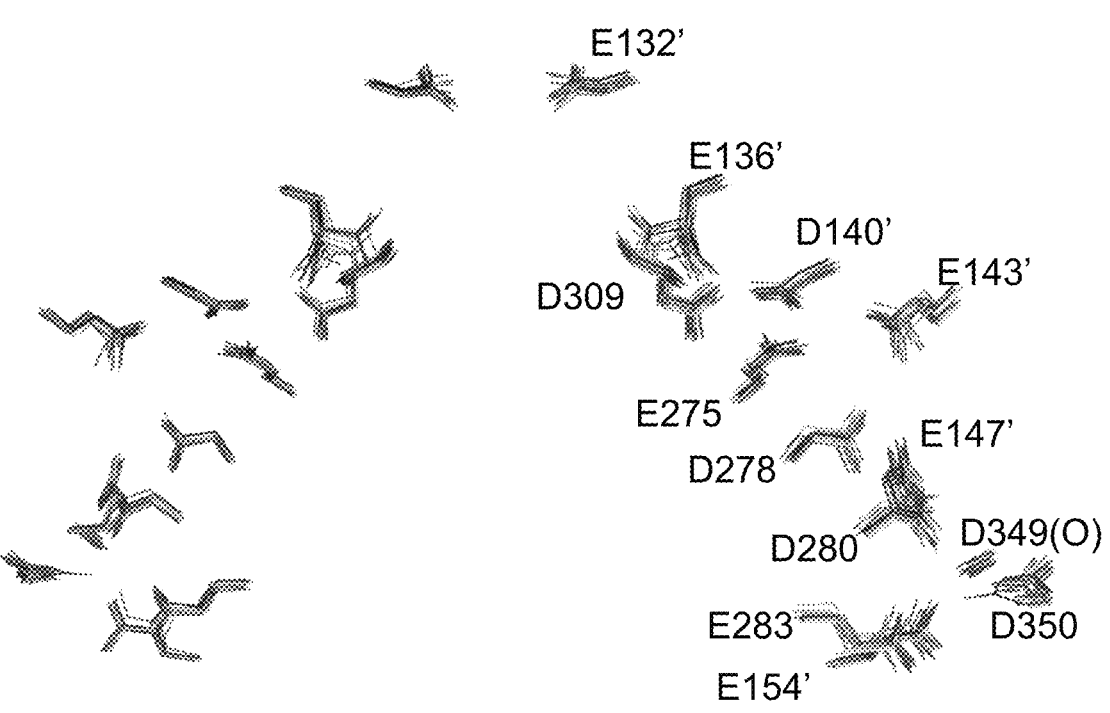

FIGS. 1A-1G and FIGS. 2A-2E were generated using PyMol. FIG. 2A is a schematic diagram illustrating a comparison of exemplary structures of superimposed seven dimers from human and rat $Ca^{2+}$ bound CSQ2 structures according to some embodiments of the present disclosure. These 14 monomers presented little structure differences with RMSD around 0.3 Å$^2$ between every two monomers (shown in FIG. 2A).

The structure of the $Ca^{2+}$ bound CSQ2 protein was analyzed. FIG. 1A is a schematic diagram illustrating an exemplary overall structure of human CSQ2 monomer complexed with calcium according to some embodiments of the present disclosure. Each monomer is comprised of three thioredoxin-like domains with the flexible C-terminal unidentified in the structures shown in FIG. 1A. Three thioredoxin domains, the N-terminal region and the C-terand FIG. 2C, CSQ2 is rich in acidic residues (Asp and Glu) at the protein surface which serve as the $Ca^{2+}$ binding ligands.

Figure 2D:
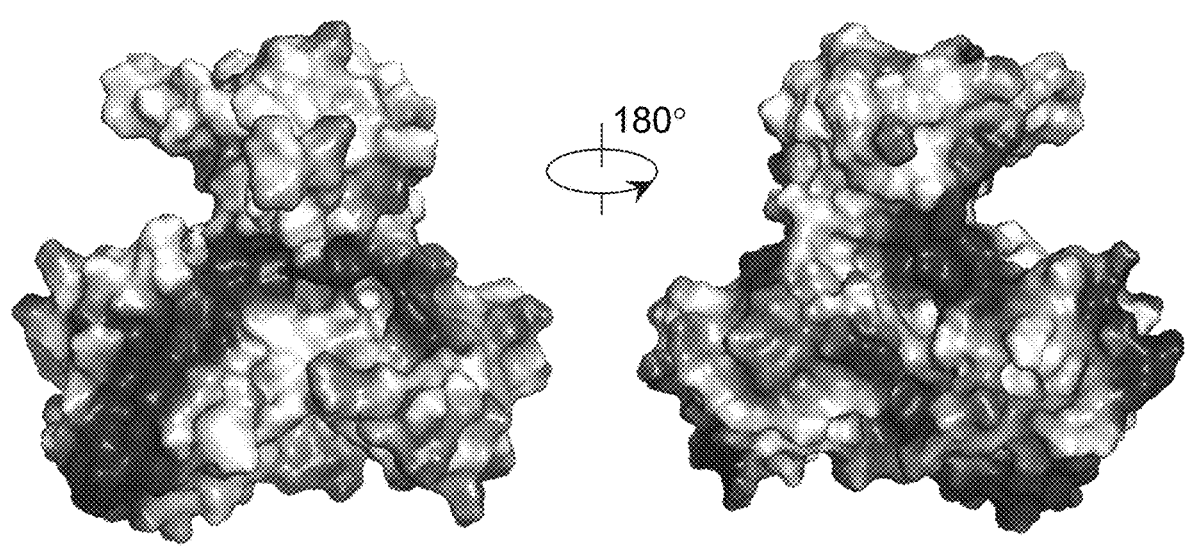
FIG. 2D is a schematic diagram illustrating the electrostatic potential surface of an exemplary rat CSQ2 monomer according to some embodiments of the present disclosure.

FIG. 1B is a schematic diagram illustrating an electrostatic potential surface of an exemplary CSQ2 monomer according to some embodiments of the present disclosure. FIG. 2D is a schematic diagram illustrating the electrostatic potential surface of an exemplary rat CSQ2 monomer according to some embodiments of the present disclosure. As shown in FIG. 1B and FIG. 2D, the acidic residues formed a negatively charged groove on the protein surface along one side of the monomer.

Figure 2E:
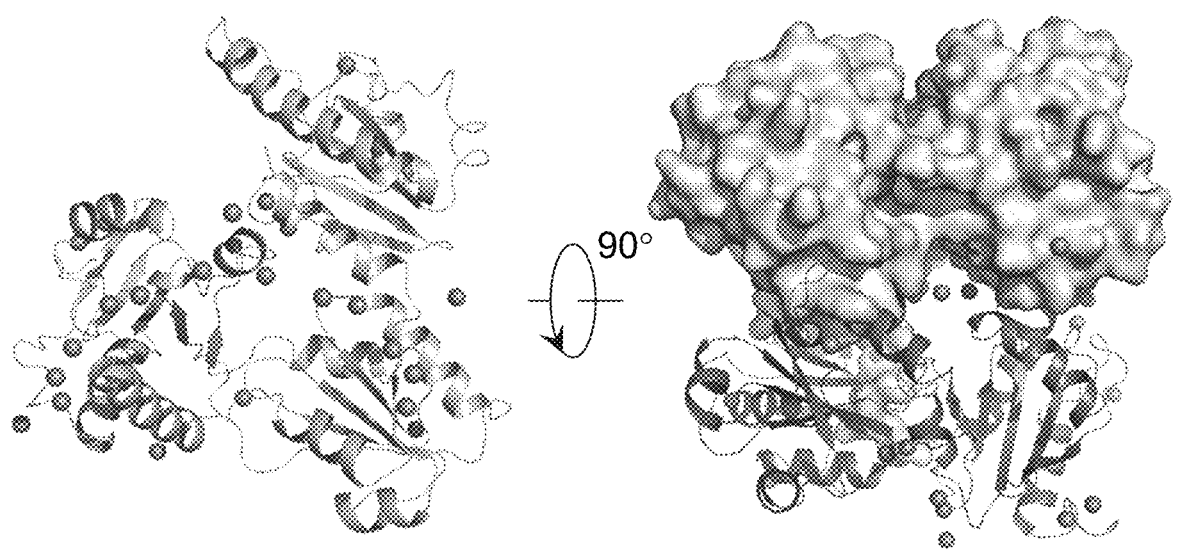
FIG. 2E is a schematic diagram illustrating the N-terminal domain exchange of a CSQ2 dimer according to some embodiments of the present disclosure.

FIG. 2E is a schematic diagram illustrating the N-terminal domain exchange of a CSQ2 dimer according to some embodiments of the present disclosure. The local C2-cymmetry axis is illustrated in FIG. 2E. In the right panel of FIG.

2E, the surface of the monomer A is shown and the structure of the monomer B is illustrated as a ribbon. As shown in FIG. 2E, the CSQ2 protein dimerizes by bridging of $Ca^{2+}$ in the groove at the dimer interface with the assistance of N-terminal exchange in a face-to-face mode.

FIG. 1C is a schematic diagram illustrating an exemplary structure of human CSQ2 dimer according to some embodiments of the present disclosure. The two CSQ2 monomers that form the dimer are illustrated as ribbons with different colors. The CSQ2 monomer on the left in FIG. 1C was referred to as monomer A and the CSQ2 monomer on the right in FIG. 1C was referred to as monomer B. Free $Ca^{2+}$ ions are illustrated by spheres marked with a relatively light color. The ones at the dimer interface are illustrated by spheres marked with a relatively dark color. The $Ca^{2+}$ ions bound at the dimer interface account for 56-60% of the total bound $Ca^{2+}$ ions.

FIG. 1D and FIG. 1E are schematic diagrams illustrating exemplary calcium ions bond at the human CSQ2 dimer interface according to some embodiments of the present disclosure. The main chain of Asp349 and side chains of the other coordinated residues are shown in sticks with ' representing for residues from monomer B. The 2Fo-Fc electron density map of human CSQ2 for the $Ca^{2+}$ ions at the interface are contoured at 1.2 σ. As shown in FIGS. 1D and 1E, the $Ca^{2+}$ ions bound at the dimer interface are designated as A to H for the monomer B and a to H for the monomer A. The distance between the $Ca^{2+}$ ions are also shown in FIG. 1E. As shown in FIG. 1D, the density of the $Ca^{2+}$ ions at the dimer interface are consecutive along the groove.

Figure 3A:
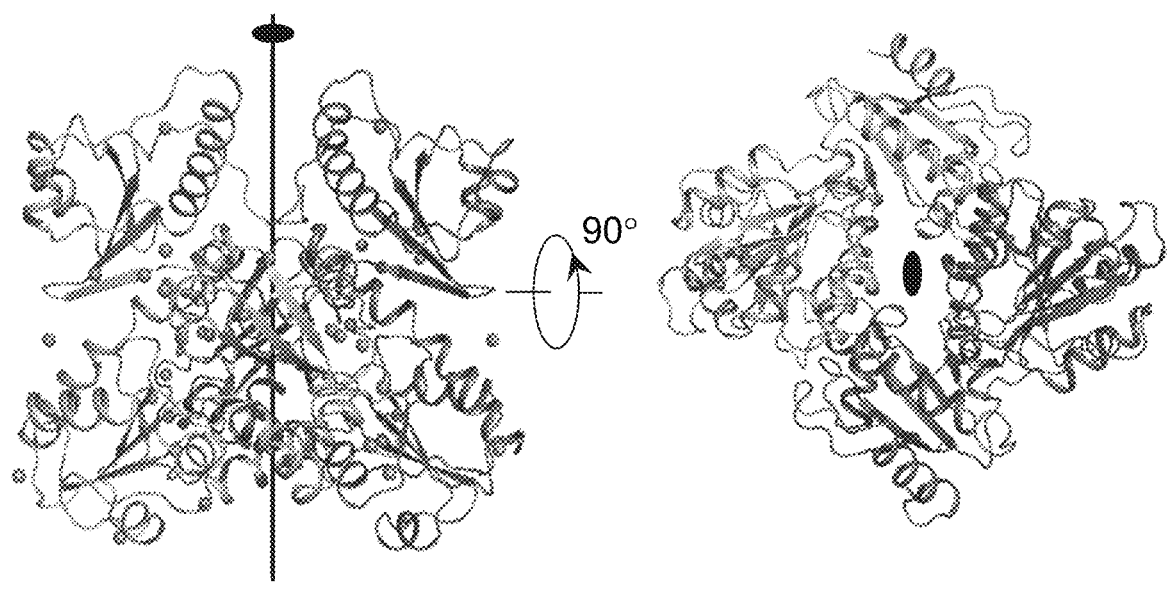
FIG. 3A is a schematic diagram illustrating a biological tunnel structure of a CSQ2 dimer according to some embodiments of the present disclosure.
Figure 3B:
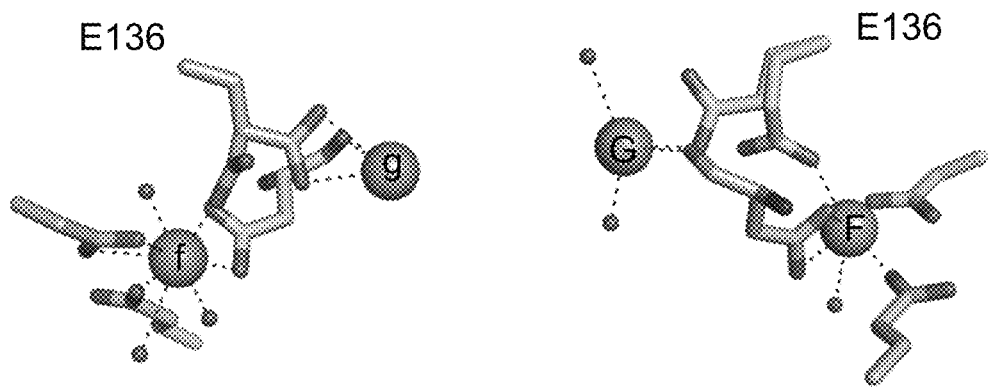
FIG. 3B is a schematic diagram illustrating an alternative conformation of Glu 136 and the coordination geometry of $Ca^{2+}$ at sites f, g, F and G, respectively, according to some embodiments of the present disclosure.
Figure 3C:
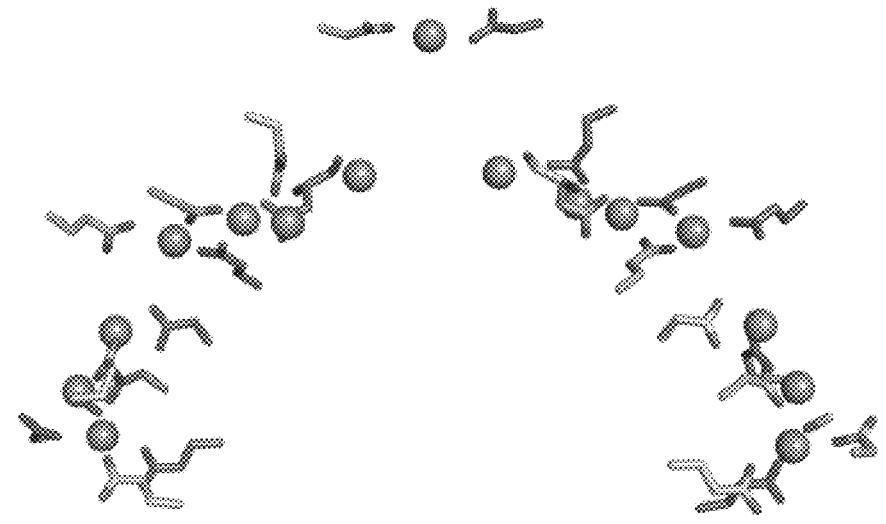
FIG. 3C is a schematic diagram illustrating $Ca^{2+}$ at the dimer interface and their coordinating ligands according to some embodiments of the present disclosure.

FIG. 3A is a schematic diagram illustrating a biological tunnel structure of a CSQ2 dimer according to some embodiments of the present disclosure. FIG. 3B is a schematic diagram illustrating an alternative conformation of Glu 136 and the coordination geometry of $Ca^{2+}$ at sites f, g, F and G, respectively, according to some embodiments of the present disclosure. FIG. 3C is a schematic diagram illustrating $Ca^{2+}$ at the dimer interface and their coordinating ligands according to some embodiments of the present disclosure. All the 7 dimers from human and rat CSQ2 and their 7 C2-symmetry related dimers are superimposed according to domain II of monomer A. Because of the local C2 symmetry axis of the CSQ2 dimer (shown in FIG. 3A), one half of the $Ca^{2+}$ ions at dimer interface is superimposable and related with the other half (shown in FIG. 1D). As shown in FIG. 1E, the $Ca^{2+}$ ions were marked by letters A to H and a to h. The $Ca^{2+}$ ions at the dimer interface were adjacent to each other. The distance between the $Ca^{2+}$ ions ranged from 2.9 Å to 9.5 Å. As shown in FIG. 1D, the density of $Ca^{2+}$ at some sites are even overlapped.

FIG. 1F and FIG. 1G are schematic diagrams illustrating a comparison of exemplary structures of the domain II of 2 dimers from human CSQ2, 5 dimers from rat CSQ2 structure and their C2-symmetry related dimers according to some embodiments of the present disclosure. As shown in FIG. 1G, the coordination ligands for $Ca^{2+}$ ions at the interface from all the superimposed dimers are shown as sticks. By superimposing all the 7 dimers and the 7 C2 symmetry related dimers together, it was found that the position of the $Ca^{2+}$ ions at each site varied (shown in FIG. 1F) according to the subtle movement of the $Ca^{2+}$ biding residues (shown in FIG. 1G and FIG. 3C). The number of coordinated ligands provided by side chains of acidic residues and water ranged from 4 to 7 (see, e.g., Table 1). The coordination geometry indicated that some of the $Ca^{2+}$ were bound at low affinity, especially $Ca^{2+}$ at sites 'G', 'g', 'H', and 'h' (shown in FIG. 1F). Besides the movement of the coordinating residues in different dimers, Asp136 which bound to the $Ca^{2+}$ at G/g sites exhibited an alternative confirmation of the side chain (shown in FIG. 1G and FIG. 3B), indicating the flexibility of the residue for facilitating the $Ca^{2+}$ binding.

Figure 4:
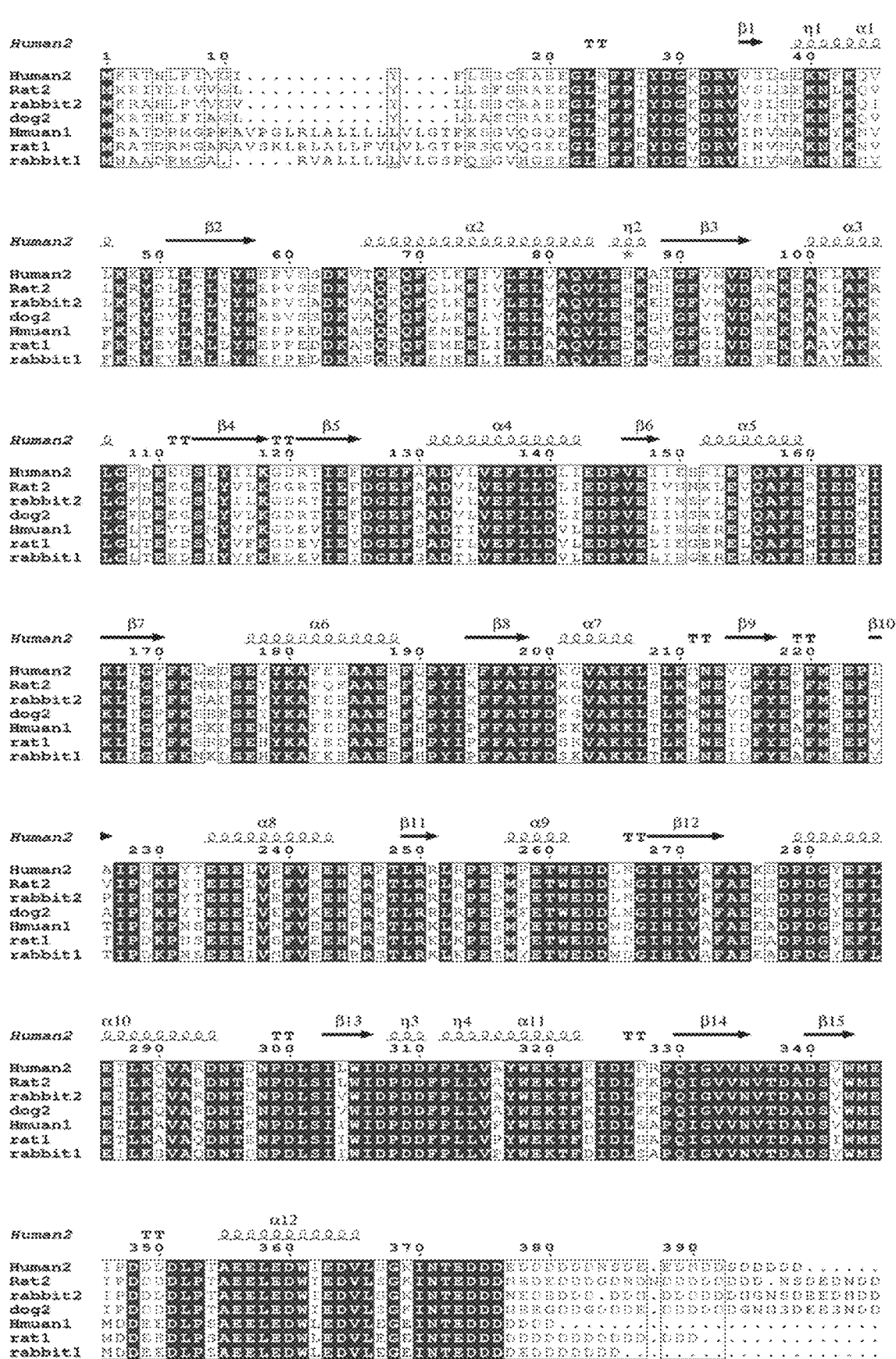
FIG. 4 is a schematic diagram illustrating a sequence alignment result of amino acid sequences of CSQ proteins from different species according to some embodiments of the present disclosure.

FIG. 4 is a schematic diagram illustrating a sequence alignment result of amino acid sequences of CSQ proteins from different species according to some embodiments of the present disclosure. The species of CSQ is indicated on the left of the aligned sequences. The amino acid sequence of the CSQ2 protein from the human (SEQ ID NO: 3, marked by "Human2"), the amino acid sequence of the CSQ2 protein from the rat (SEQ ID NO: 4, marked by "Rat2"), the amino acid sequence of the CSQ2 protein from the rabbit (SEQ ID NO: 5, marked by "rabbit2"), the amino acid sequence of the CSQ2 protein from the dog (SEQ ID NO: 6, marked by "dog2") the amino acid sequence of the CSQ1 protein from the human (SEQ ID NO: 7, marked by "Human1"), the amino acid sequence of the CSQ1 protein from the rat (SEQ ID NO: 8, marked by "rat1"), and the amino acid sequence of the CSQ1 protein from the rabbit (SEQ ID NO: 9, marked by "rabbit1") were compared. Secondary structural elements of the human CSQ2 are indicated above the amino acid sequences. Invariant amino acids are shaded in a dark color and the conserve amino acids are boxed. The $Ca^{2+}$ coordinating residues are indicated by black dots. As can be seen from FIG. 4, Rat CSQ2 consists of 108 negatively charged residues (Asp and Glu) which accounts for 27.4% of all the residues. These Asp and Glu are located at the protein surface, making the protein surface highly negatively charged, which is suitable for calcium binding (shown in FIG. 1B and FIG. 2D). The C terminal of CSQ2, which is flexible and not illustrated in FIGS. 1A-1G and FIGS. 2A-2E, contains 35 negatively charged residues in total 38 residues, accounting for 32.4% of all the negatively charged residues. For the other negatively charged residues, 36 residues (46.1%) coordinate $Ca^{2+}$, in which 13 residues (37.1%) of the coordinating residues are located at the dimer interface.

Example 2 Å Cross-Like Tunnel Through the Dimer Interface

Figure 5B:
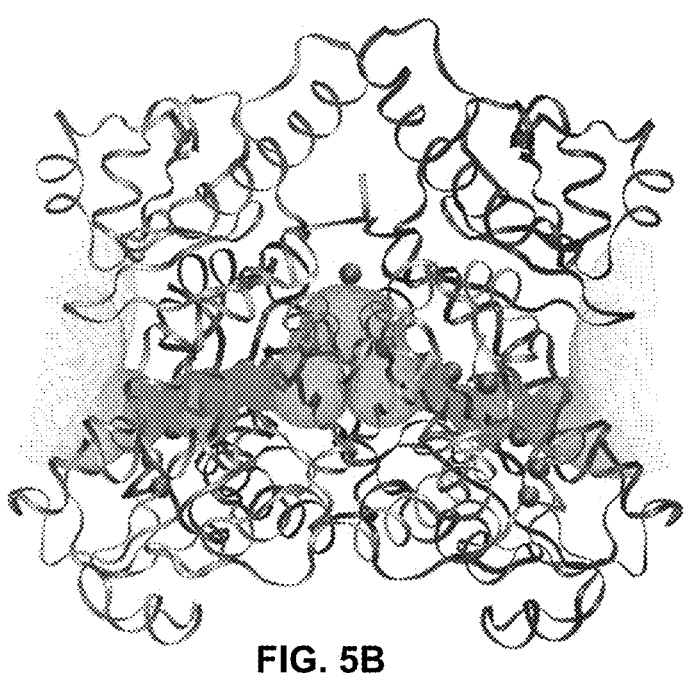
FIG. 5B is a schematic diagram illustrating the permeation pass of the human CSQ2 dimer according to some embodiments of the present disclosure.

FIG. 5A is a schematic diagram illustrating cut-open views of the electrostatic potential for an exemplary human CSQ2 dimer according to some embodiments of the present disclosure. FIG. 5B is a schematic diagram illustrating the permeation pass of the human CSQ2 dimer according to some embodiments of the present disclosure. The permeation pass of the human CSQ2 dimer was determined by HOLE (see, e.g., O. S. Smart, J. G. Neduvelil, X. Wang, B. A. Wallace, M. S. Sansom, HOLE: a program for the analysis of the pore dimensions of ion channel structural models. *J. Mol. Graph.* 14, 354-360 (1996). doi: 10.1016/S0263-7855(97)00009-X), and was shown by gray dots. As shown in FIG. 5A and FIG. 5B, the dimer exhibited a tunnel through the dimer interface. The helices 4, 5 and 10 (shown in FIG. 4) from two monomers contribute to the negatively charged residues (shown in FIG. 1D) to form the tunnel (shown in FIG. 5A).

Figure 5C:
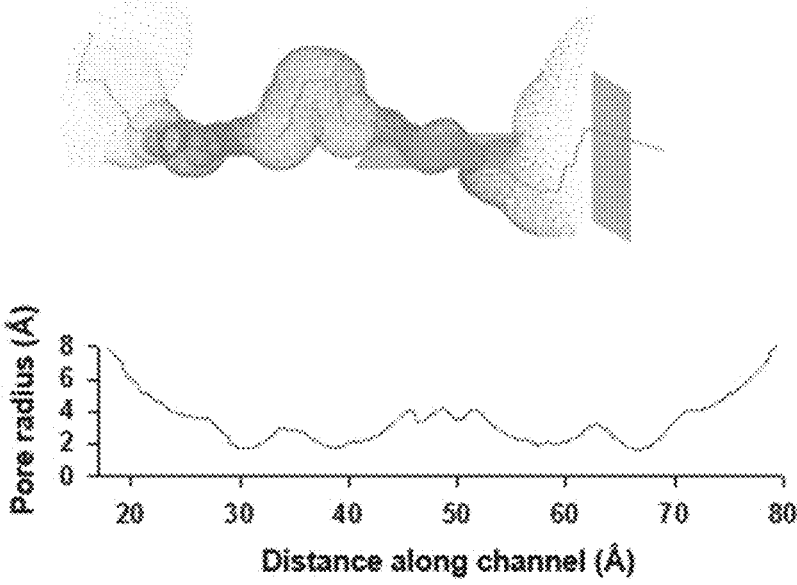
FIG. 5C is an analytical diagram illustrating the pore radii of the tunnel according to some embodiments of the present disclosure.

FIG. 5C is an analytical diagram illustrating the pore radii of the tunnel according to some embodiments of the present disclosure. The figures of the permeation pass determined by HOLE (e.g., FIG. 5B and the upper panel of FIG. 5C) were generated using visual molecular dynamics (VMD). As shown in FIG. 5C, the tunnel had a length of about 60 Å with 2 wide mouths and 4 narrow regions. The smallest radius of the tunnel was 1.6 Å at the side chain of Asp147 around the site E of $Ca^{2+}$ (shown in FIG. 5C and FIG. 1D), which may allow the $Ca^{2+}$ ion to permeate in a single file manner. The radius of the tunnel at the site D of $Ca^{2+}$ was 1.7 Å, which is coordinated with Asp 309, Asp 140, Glu143 and Asp275 (shown in FIG. 1D). The small radius of the tunnel around these sites implies the critical role of the key residues of the CSQ2 protein in $Ca^{2+}$ binding.

Figure 5D:
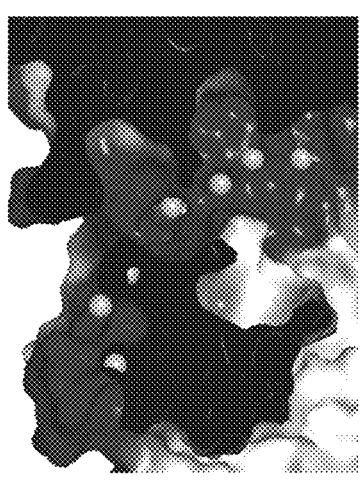
FIG. 5D and FIG. 5E are schematic diagrams illustrating a cut-open top view and a cut-open side view of the electrostatic potentials of the tunnel of an exemplary CSQ2 dimer according to some embodiments of the present disclosure.
Figure 5E:
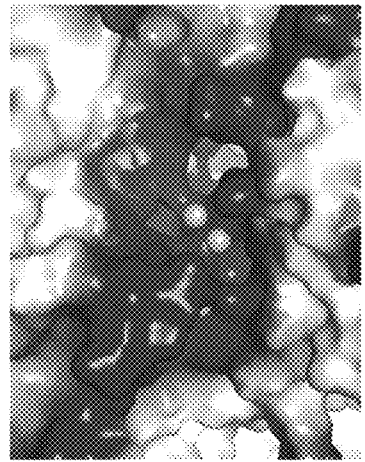

FIG. 5D and FIG. 5E are schematic diagrams illustrating a cut-open top view and a cut-open side view of the electrostatic potentials of a tunnel of an exemplary CSQ2 dimer according to some embodiments of the present disclosure. As shown in FIG. 5D and FIG. 5E, unlike the classical ion channels, the tunnel was asymmetry and had an irregular shape. As shown in FIG. 5E, a total number of 14 $Ca^{2+}$ ions in the tunnel are stick to the negative residues but not the center of the tunnel.

FIG. 6 is a schematic diagram illustrating an exemplary structure of a CSQ2 polymer formed by a plurality of CSQ2 dimers according to some embodiments of the present disclosure. As shown in FIG. 6, a plurality of CSQ2 dimers (e.g., the dimers 1, 2, 3, and 4) were organized into the CSQ2 polymer in the crystal lattice. The $Ca^{2+}$ tunnels of the CSQ2 dimers were connected and a long continuous $Ca^{2+}$ tunnel was formed in the CSQ2 polymer. The continuous $Ca^{2+}$ tunnel throughout the CSQ2 polymer was obtained using the Caver software and is shown as gray dots.

Example 3 the Conductance of CSQ2 Dimer In-Vitro

Figure 7A:
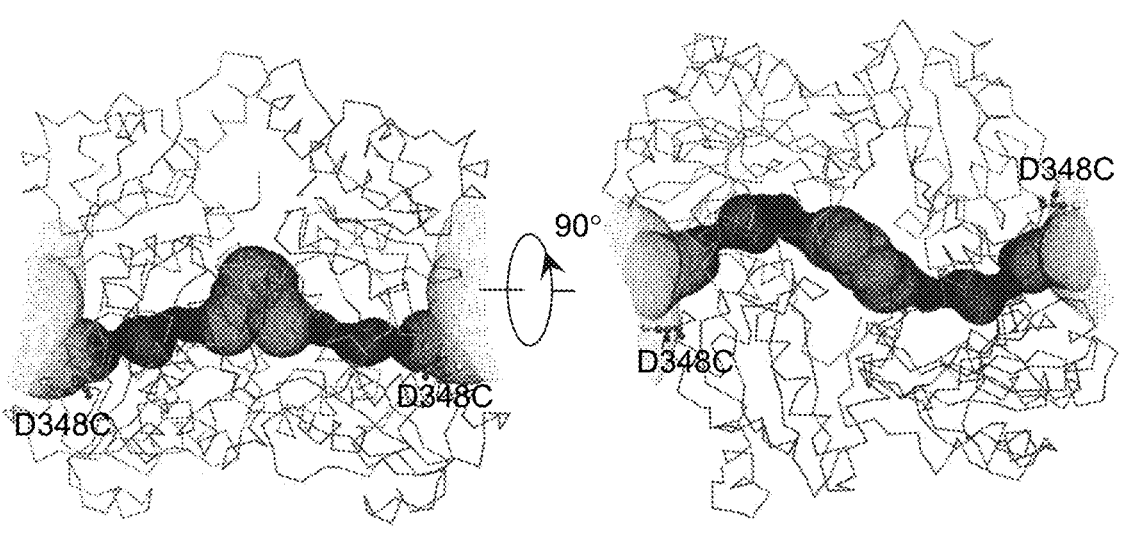
FIG. 7A is a schematic diagram illustrating the position of D348C mutation of a CSQ2 protein according to some embodiments of the present disclosure.
Figure 7B:
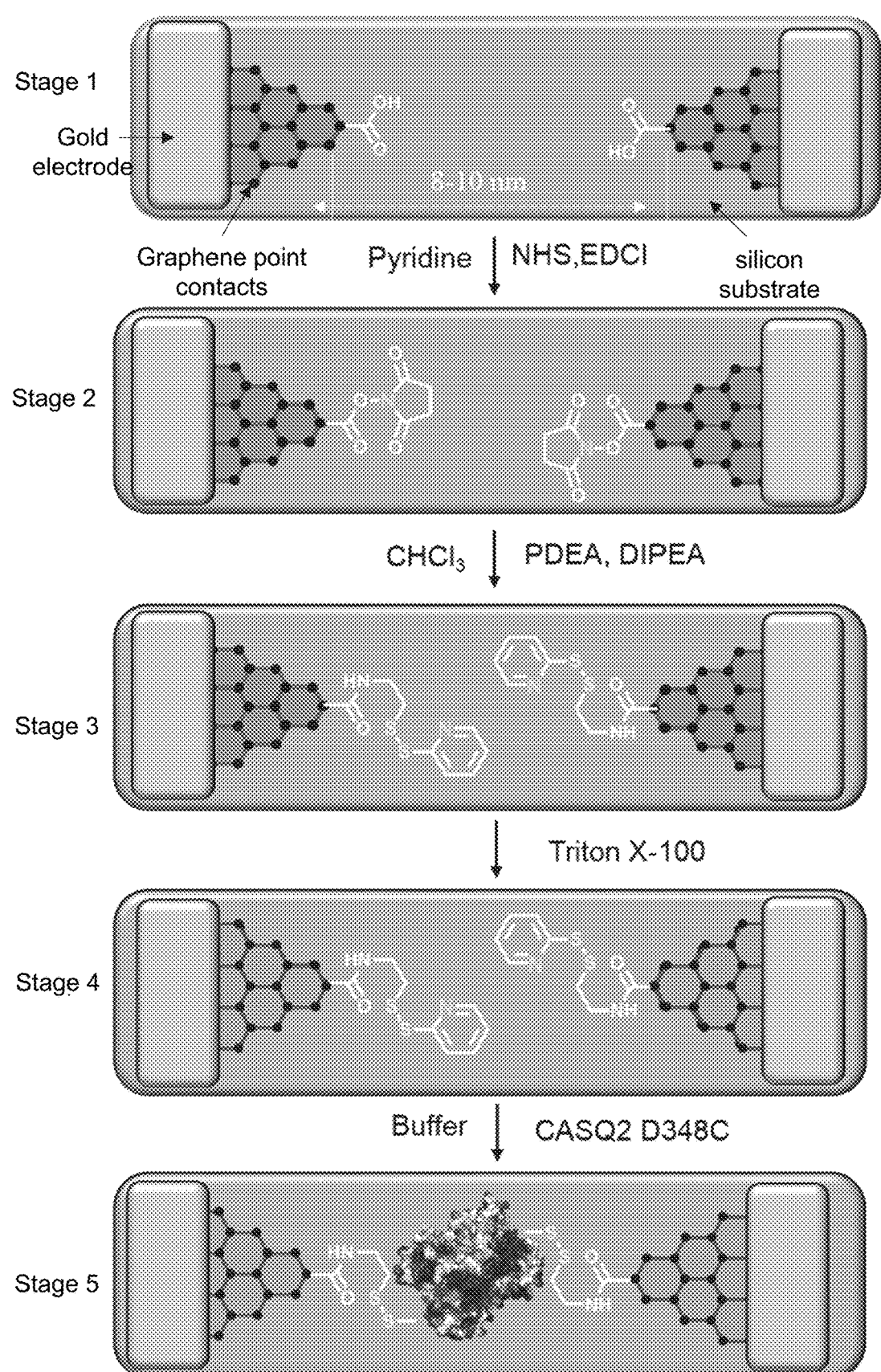
FIG. 7B is a schematic diagram illustrating an exemplary process of connecting a CSQ2 dimer to a device in a nano-gap of the device according to some embodiments of the present disclosure.
Figure 7C:
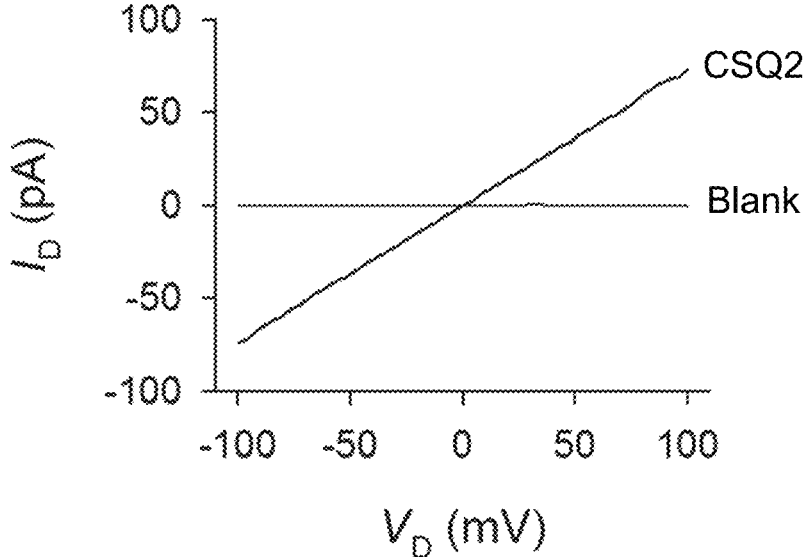
FIG. 7C is an analytical diagram illustrating the conductance of an exemplary device and the device connected with the CSQ2 dimer according to some embodiments of the present disclosure.
Figure 8A:
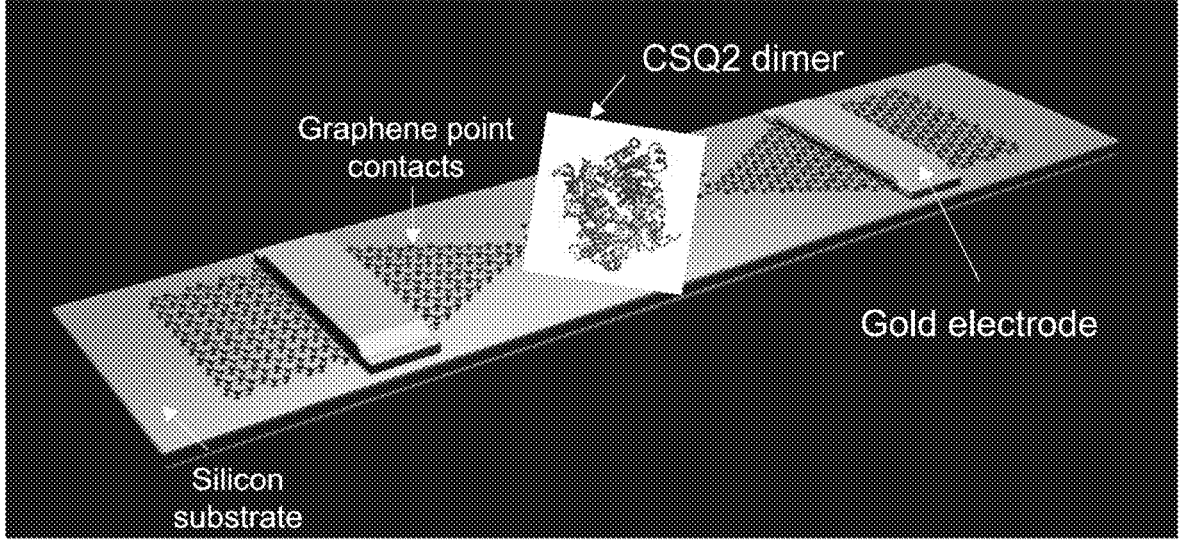
FIG. 8A is a schematic diagram illustrating an exemplary device connected with the CSQ2 dimer according to some embodiments of the present disclosure.

To detect the conductance of CSQ2 dimer, a single-molecule electrical approach was applied. FIG. 7A is a schematic diagram illustrating the position of D348C mutation of a CSQ2 protein according to some embodiments of the present disclosure. Asp348 at the mouth of the tunnel was mutated to Cys. Since the tunnel is C2-symmetry related, mutation of Asp to Cys of 348 amino acid of human CSQ2 resulted in 2 sulfydryl groups at both mouths of the tunnel, which facilitated the connection of a CSQ2 dimer (with a size of 6*6*6 nm) to the a nano-gap of a device (with 8-10 nm in width) by disulfide bonds. FIG. 8A is a schematic diagram illustrating an exemplary device connected with the CSQ2 dimer according to some embodiments of the present disclosure. The CSQ2 dimer (illustrated as a ribbon structure) was connected with modified graphene point contacts. The graphene point contacts were deployed on a silicon substrate and connected to a gold electrode. FIG. 7B is a schematic diagram illustrating an exemplary process of connecting a CSQ2 dimer to a device in a nano-gap of the device according to some embodiments of the present disclosure. The process of connecting the CSQ2 dimer to the device generally included 5 stages. In stage 1, a device with a nano-gap having the width of 8-10 nm was fabricated. As shown in FIG. 7B, the graphene point contacts were connected to carboxylic groups on both sides. In stage 2, the device was treated with pyridine, N-Hydroxysuccinimide (NHS), and 1-Ethyl-3-(3-dimethylaminopropyl)carbodiimide (EDCI). In stage 3, the device was immersed in a $CHCl_3$ solution containing PDEA and DIPEA. In stage 4, a triton X-100 polymer coating was added on the device for the protection for the electrode. In stage 5, the device was immersed in a buffer containing the CSQ2 D348C protein mutant for the connection of a CSQ2 dimer to the device. The device connected with the CSQ2 dimer is also referred to as a CSQ2-device. FIG. 7C is an analytical diagram illustrating the conductance of an exemplary device and the device connected with the CSQ2 dimer according to some embodiments of the present disclosure. As shown in FIG. 7C, the successful establishment of the CSQ2-device was verified by the increase of conductance at solid-phase compared with the device alone.

Figure 8B:
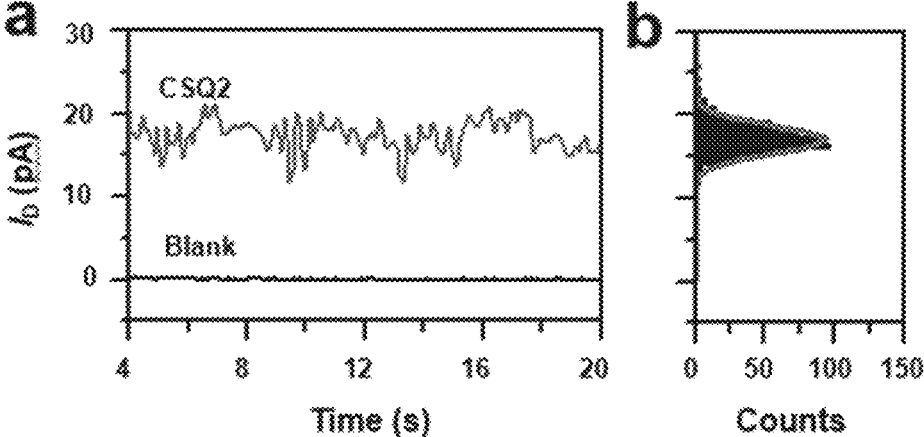
FIG. 8B is a group of analytical diagrams illustrating the conductance of an exemplary device connected with the CSQ2 dimer according to some embodiments of the present disclosure.
Figure 8B:
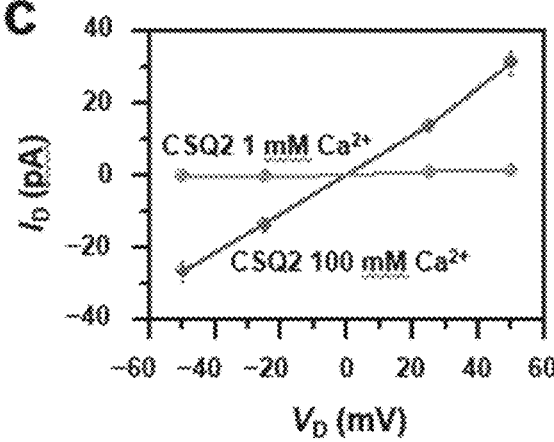

Time dependent electrical measurements of the devices were carried out in a test buffer. FIG. 8B is a group of analytical diagrams illustrating the conductance of an exemplary device connected with the CSQ2 dimer according to some embodiments of the present disclosure. The current-time (1-t) relationship of the devices at different bias voltages with and without CSQ2 were measured in a solution containing 1 mM $Ca^{2+}$ and 1.2 mM $Mg^{2+}$. Section (a) of FIG. 8B is the 1-t curves of the devices with or without CSQ2 immobilized. The 1-t curves were recorded with a holding time of 20 s for electrochemical equilibration. When a small bias of 25 mV was applied between the source and drain electrodes, a serious of current spikes were observed for the device with CSQ2 immobilized (FIG. 8B section (a)). The result current count histogram (FIG. 8B section (b)) revealed a Gaussian distribution centered at 15 pA. In contrast, in completely-cut SMJs without a CSQ2 dimer, the current was approximately zero under the same measurement conditions (FIG. 8B section (a)), indicating that the current depended on the presence of CSQ2. Whether CSQ2 dimerization was required for the current was further tested. The $Ca^{2+}$ concentration in another test buffer was 100 nM, which induced dissociation of the CSQ2 dimers into monomers. The current-voltage (1-V) relationship of CSQ2-immobilized SMJs at the bias voltages of ±25 and ±50 mV was shown in FIG. 8B section (c). The current in CSQ2-immobilized SMJs was nearly zero (FIG. 8B section (c) orange line), which was similar to that observed in SMJs without the CSQ2 dimer. These results indicate that the current was mediated exclusively by the CSQ2 dimer.

Figure 9A:
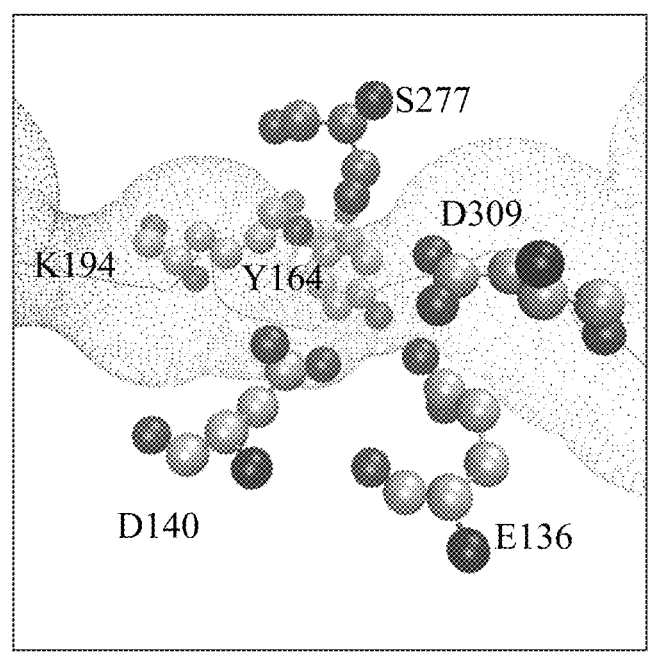
FIG. 9A is a schematic diagram illustrating the bottleneck of an exemplary CSQ2 tunnel and amino acid residues surrounding the CSQ2 tunnel according to some embodiments of the present disclosure.

Example 4 Mutation of the Tunnel Forming and Calcium Coordinating Residue Asp309 Aborted Calcium Tunneling In-Vitro and In-Vivo To further confirm the $Ca^{2+}$ tunneling of CSQ2, the key residue Asp309 was mutated to Asn. FIG. 9A is a schematic diagram illustrating the bottleneck of an exemplary CSQ2 tunnel and amino acid residues surrounding the CSQ2 tunnel according to some embodiments of the present disclosure. The residues surrounding the tunnel were depicted as spheres. Asp140, Asp275, Ser277, water bound Lys195, and Asp309 formed the narrow region of the tunnel, with the side chain of Asp309 gated $Ca^{2+}$ transportation from the bottleneck at site E to the cross center of the tunnel.

Figure 9B:
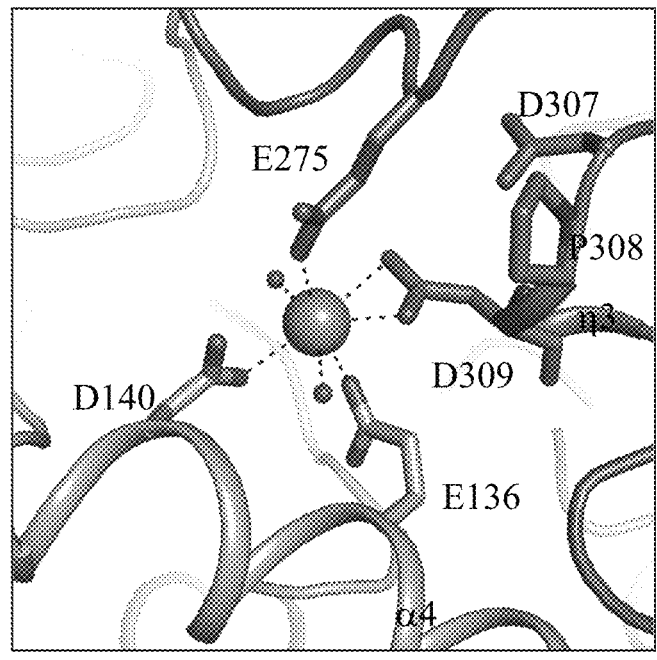
FIG. 9B is a schematic diagram illustrating the $Ca^{2+}$ coordination geometry (site E) at the bottleneck according to some embodiments of the present disclosure.

FIG. 9B is a schematic diagram illustrating the $Ca^{2+}$ coordination geometry (site E) at the bottleneck according to some embodiments of the present disclosure. The contributing residues and catecholaminergic polymorphic ventricular tachycardia 2 (CPVT2) causing residues (Asp307 and Pro308) are shown as sticks in FIG. 9B. The coordinated water is shown as a sphere. The side chain of Asp309, Asp140 and Asp275 coordinated $Ca^{2+}$ with a bipyramidal geometry at site E. Asp 307, Pro308, and Asp309 form a 3-10 helix, which is a CPVT mutation hot spot.

Figure 10A:
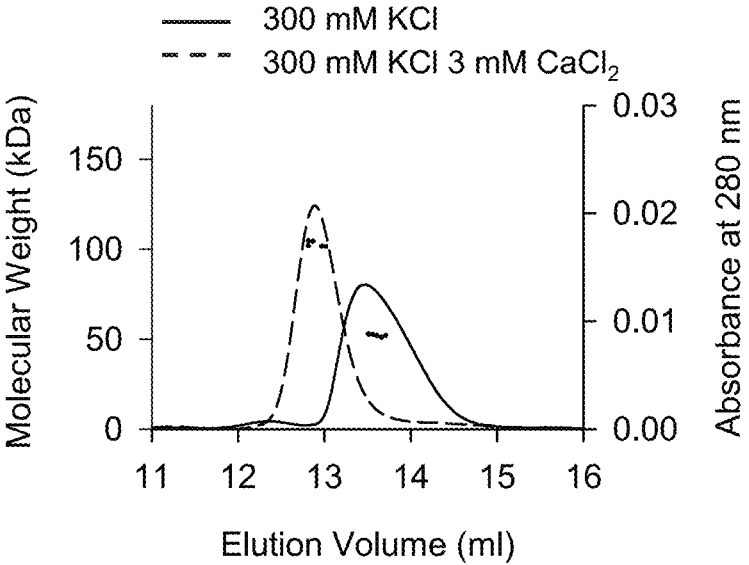
FIG. 10A is an analytical diagram illustrating the result of a liquid chromatography-multi angle light scattering (LC-MALS) test of $CSQ2^{WT}$ according to some embodiments of the present disclosure.
Figure 10B:
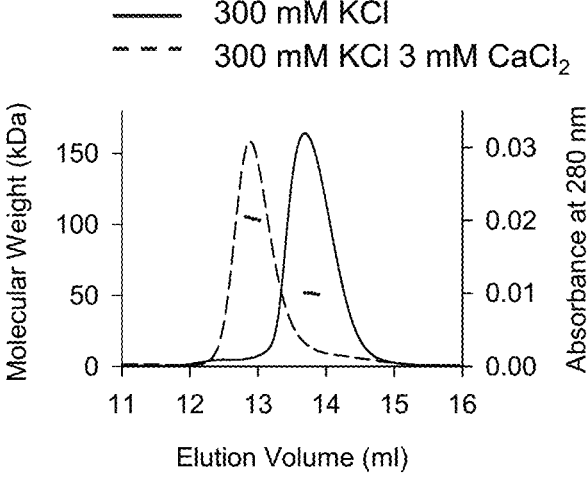
FIG. 10B is an analytical diagram illustrating the result of an LC-MALS test of $CSQ2^{D309N}$ according to some embodiments of the present disclosure.
Figure 10C:
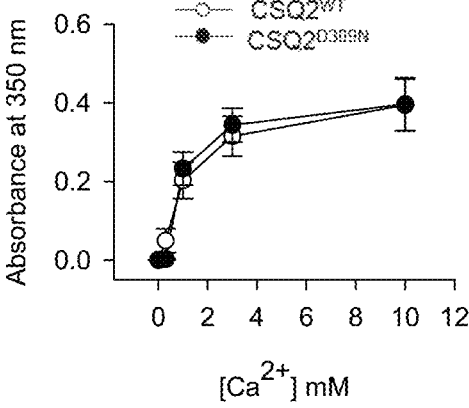
FIG. 10C is an analytical diagram illustrating the result of a turbidity assay of $CSQ2^{WT}$ (black circle) and $CSQ2^{D309N}$ (black dots) according to some embodiments of the present disclosure.

FIG. 10A is an analytical diagram illustrating the result of a liquid chromatography-multi angle light scattering (LC-MALS) test of $CSQ2^{WT}$ according to some embodiments of the present disclosure. FIG. 10B is an analytical diagram illustrating the result of an LC-MALS test of $CSQ2^{D309N}$ according to some embodiments of the present disclosure. Plotting of size-exclusion chromatography elution data of $CSQ2^{WT}$ and $GSQ2^{D309N}$ in calcium free buffer (solid line) and calcium containing buffer (dashed line) was shown in FIGS. 10A and 10B, respectively. The molecular weight was plotted as dots. FIG. 10C is an analytical diagram illustrating the result of a turbidity assay of $CSQ2^{WT}$ (black circle) and $CSQ2^{D309N}$ (black dots) according to some embodiments of the present disclosure. As shown in FIGS. 10A, 10B, and 10C, the D309N mutation did not impair the $Ca^{2+}$ induced dimerization and the polymerization of the CSQ2 protein.

Figure 9C:
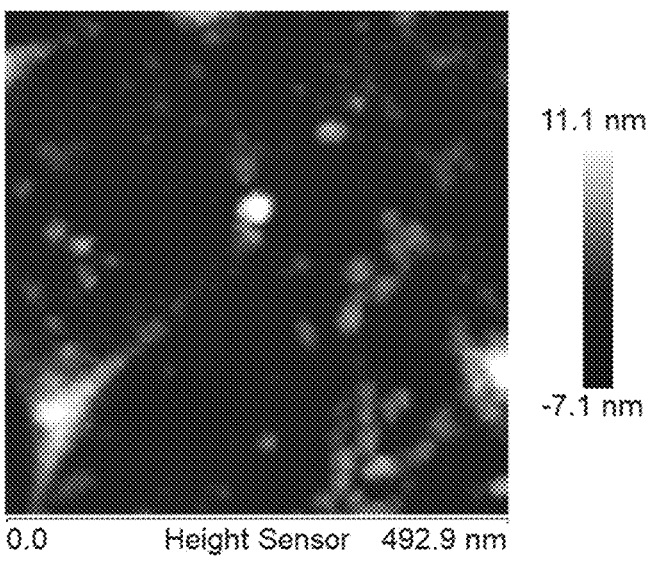
FIG. 9C is an atomic force microscope (AFM) graph of a device connected with wild type CSQ2 according to some embodiments of the present disclosure.
Figure 9D:
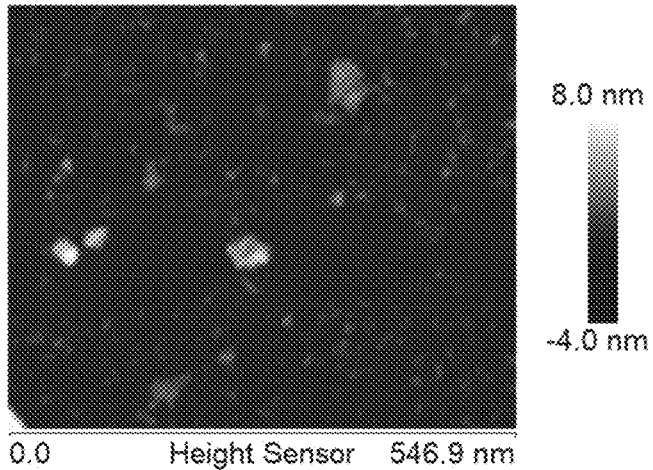
FIG. 9D is an AFM graph of a device connected with a CSQ2 D309N mutant according to some embodiments of the present disclosure.

FIG. 9C is an atomic force microscope (AFM) graph of a device connected with wild type CSQ2 according to some embodiments of the present disclosure. The device connected with the wild type CSQ2 is also referred to as a "$CSQ2^{WT}$-device". FIG. 9D is an AFM graph of a device connected with a CSQ2 D309N mutant according to some embodiments of the present disclosure. The device connected with the CSQ2 D309N mutant is also referred to as a "$CSQ2^{D309N}$-device". The successful connection of $CSQ2^{WT}$ and $GSQ2^{D309N}$ to the device was confirmed by an l-V test at solid-phase shown in FIG. 7C and the AFM graphs shown in FIG. 9C and FIG. 9D.

Figure 9E:
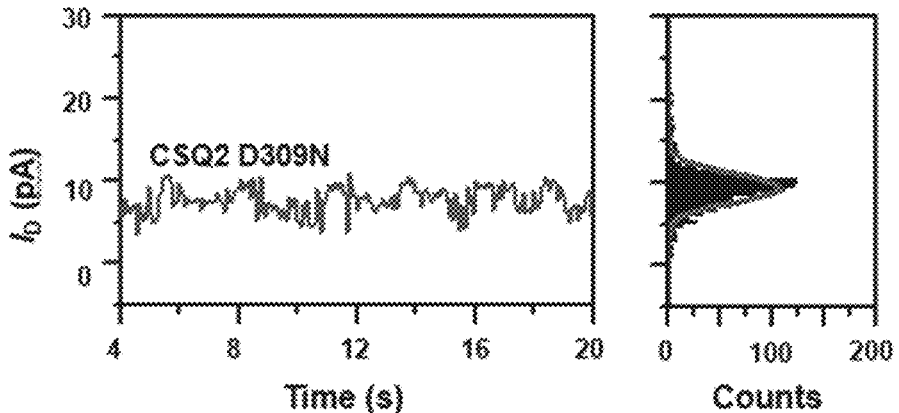
FIG. 9E is a schematic diagram illustrating the l-t curve of the $CSQ2^{D309N}$-device according to some embodiments of the present disclosure.

FIG. 9E is a schematic diagram illustrating the l-t curve of the $CSQ2^{D309N}$-device according to some embodiments of the present disclosure. As shown in FIG. 9E, the $CSQ2^{D309N}$-device showed decreased current at a voltage of 25 mV, which demonstrates that the $Ca^{2+}$ conductance was decreased compared with the wild type CSQ2.

It should be noted that the examples described above are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lies in less than all features of a single foregoing disclosed embodiment.

We claim:

1. An in vitro electrical conductor comprising a plurality of Calsequestrin (CSQ) protein molecules, wherein the CSQ protein molecules are connected to an electrode, wherein the CSQ protein molecules include either a CSQ1 molecule or a CSQ2 molecule, and at least one of the CSQ protein molecules comprises a mutation from an amino acid residue to C (Cys), which is connected to the electrode via a disulfide bond.

2. The in vitro electrical conductor of claim 1, wherein the CSQ protein molecules include CSQ1 molecules that use intermolecular interactions to form a tendril or a network structure.

3. The in vitro electrical conductor of claim 1, wherein the CSQ protein molecules form a biological tunnel structure comprising a CSQ protein dimer, wherein the CSQ protein dimer includes two CSQ molecules either of which is a CSQ1 molecule or a CSQ2 molecule.

4. The in vitro electrical conductor of claim 3, wherein the CSQ protein dimer includes two CSQ2 molecules using an intermolecular interaction to form the biological tunnel structure.

5. The in vitro electrical conductor of claim 4, wherein at least one of the CSQ2 protein molecules includes an amino acid sequence with at least 95% similarity to SEQ ID NO: 1, wherein the SEQ ID NO: 1 consists of human CSQ2 protein sequence without amino acids 1-19.

6. The in vitro electrical conductor of claim 5, wherein at least one of the CSQ2 protein molecules consists of an amino acid sequence with at least 99% similarity to SEQ ID NO: 1, which consists of human CSQ2 protein sequence without amino acids 1-19.

7. The in vitro electrical conductor of claim 4, wherein at least one of the CSQ2 protein molecules includes an amino acid sequence with at least 95% similarity to SEQ ID NO: 2, wherein the SEQ ID NO: 2 consists of rat CSQ2 protein sequence without amino acids 1-19.

8. The in vitro electrical conductor of claim 7, wherein at least one of the CSQ2 protein molecules consists of an amino acid sequence with at least 99% similarity to SEQ ID NO: 2, which consists of rat CSQ2 protein sequence without amino acids 1-19.

9. The in vitro electrical conductor of claim 4, wherein at least one of the CSQ2 protein molecules comprises one or more amino acid mutations that enhance or reduce conductivity of the biological tunnel structure.

10. The in vitro electrical conductor of claim 4, wherein the in vitro electrical conductor is in a medium with a calcium ion concentration that facilitates CSQ2 protein dimerization.

11. The in vitro electrical conductor of claim 1, wherein the in vitro electrical conductor is an ionic conductor configured for conduction of cations.

12. The in vitro electrical conductor of claim 1, wherein the at least one CSQ protein molecule is a CSQ2 protein molecule and the mutation to C (Cys) comprises a D (Asp) to C (Cys) mutation, which facilitates a connection between the CSQ protein molecules to the electrode.

13. The in vitro electrical conductor of claim 12, wherein the D (Asp) to C (Cys) mutation is at amino acid position 348 as defined in a full-length human or rat CSQ2 protein sequence.

14. The in vitro electrical conductor of claim 11, wherein the cations are calcium ions.

15. An electrical device comprising an in vitro electrical conductor, wherein the electrical conductor comprises a plurality of Calsequestrin (CSQ) protein molecules, wherein the CSQ protein molecules are connected to an electrode, wherein the CSQ Protein molecules include either a CSQ1 molecule or a CSQ2 molecule, and at least one of the CSQ Protein molecules comprises a mutation from an amino acid residue to C (Cys), which is connected to the electrode via a disulfide bond.

16. The electrical device of claim 15, further comprising:
a cation source or sink, comprising a composition capable of donating or accepting cations.

17. The electrical device of claim 16, further comprising an encasing structure which isolates the cation source or sink from an external environment.

18. The electrical device of claim 15, wherein the electrode includes:
a gating electrode in contact with or in proximity to the CSQ Protein molecules, wherein the gating electrode is configured to apply sufficient electric field to induce electrical currents through the in vitro electrical conductor.

* * * * *